(12) United States Patent
Miyadera et al.

(10) Patent No.: US 6,255,314 B1
(45) Date of Patent: *Jul. 3, 2001

(54) CANCEROUS METASTASIS INHIBITORS CONTAINING URACIL DERIVATIVES

(75) Inventors: Kazutaka Miyadera, Hanno; Tomohiro Emura, Iruma; Konstanty Wierzba, Sayama; Yuji Yamada, Higashiyamato, all of (JP)

(73) Assignee: Taiho Charmaceutical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/077,209

(22) PCT Filed: Sep. 22, 1997

(86) PCT No.: PCT/JP97/03355

§ 371 Date: May 26, 1998

§ 102(e) Date: May 26, 1998

(87) PCT Pub. No.: WO98/13045

PCT Pub. Date: Apr. 2, 1998

(30) Foreign Application Priority Data

Sep. 24, 1996 (JP) .................................................... 8-251303

(51) Int. Cl.$^7$ ....................... A61K 31/513; A61P 35/04; C07D 239/52
(52) U.S. Cl. ........................ 514/274; 544/295; 544/296; 544/310; 544/311
(58) Field of Search .................................. 544/295, 296, 544/310, 311; 514/274

(56) References Cited

U.S. PATENT DOCUMENTS 5,744,475 * 4/1998 Yano et al. ........................... 544/309

FOREIGN PATENT DOCUMENTS 07188023  7/1995 (JP) .

* cited by examiner

Primary Examiner—Richard L. Raymond
Assistant Examiner—Venkataraman Balasubramanian
(74) Attorney, Agent, or Firm—Sughrue, Mion, Zinn, Macpeak & Seas, PLLC

(57) ABSTRACT

This invention provides a drug which has inhibitory activities against thymidine phosphorylase and inhibits metastasis of a cancer. Specifically, this invention relates to a cancerous metastasis inhibitor comprising, as an active ingredient, a uracil derivative represented by the following formula (1):

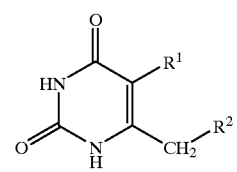

(1)

wherein $R^1$ represents a chlorine, bromine or iodine atom or a cyano or lower alkyl group and $R^2$ represents a substituted or unsubstituted 4–8 membered hetero-cyclic group having nitrogen atoms or a substituted or unsubstituted amidinothio, guanidino, (lower alkyl)amidino, amino or like group, or a salt thereof.

7 Claims, No Drawings

US 6,255,314 B1

CANCEROUS METASTASIS INHIBITORS CONTAINING URACIL DERIVATIVES

TECHNICAL FIELD

This invention relates to a cancerous metastasis inhibitor which contains a uracil derivative having thymidine phosphorylase inhibiting activity.

BACKGROUND ART

Cancer treatments have achieved an innovative level of progress in recent years and, especially, an improvement in the success rate of primary carcinoma removal by surgery or radiotherapy has significantly contributed to the progress in cancer treatments. Nonetheless, there are not but a few cases of death by relapse due to metastases of cancers in spite of complete removal of primary carcinomas. A limitation is therefore imposed on the complete prevention of advances of cancers by surgery or radiotherapy.

There is accordingly a growing recognition that the prevention of metastasis of a cancer is an important theme to be achieved for the treatment of the cancer, and clinical tests of cancerous metastasis inhibitors are now under way in the United States, Great Britain, etc.

As a mechanism of hematogenous metastasis of a cancer, the metastasis is assumed to take place through a process which comprises (1) growth of carcinoma cells in a primary carcinoma lesion, (2) development of blood vessels, (3) infiltration of developed blood vessels by malignant carcinoma cells, followed by their penetration into the blood vessels, (4) circulation through the body, (5) arrival at and bonding to a target site, (6) infiltration to the outside of the blood vessels, (7) growth in a target organ, and (8) formation of a metastasized lesion.

As a cancerous metastasis inhibitor, it is generally desirable not only to prevent metastasis of carcinoma cells beforehand but also to prevent proliferation and metastasis of a small metastasized lesion already formed. Those currently available as chemotherapeutic agents for cancers (antitumor agents) on the market are used as drugs effective for the phase (1) in that they exhibit direct growth inhibition and cytocidal activity against carcinoma cells while bringing about size reductions of tumors. They are however not satisfactory drugs as cancerous metastasis inhibitors in that they cause various side effects led by myelotoxicity and exhibit substantially no activity against the other metastasis phases.

Accordingly, drugs of such a new type as having less side effects and permitting long-term administration in view of the process of metastasis are highly valued as cancerous metastasis inhibitors. Clinically, there is also a demand for such drugs.

The blood vessel development phase (2) has therefore been attracting interests as an important target phase for the inhibition of metastasis in recent years in that, except for the growth of a cancer, it takes place only in special cases such as wound healing, resulting in active developments of angiogenesis-inhibiting drugs as metastasis inhibitors.

Various factors are considered to take part in angiogenesis. Platelet-derived endothelial cell growth factor (PD-ECGF) [Nature, 338, 557–562 (1989)], one of such factors, has been reported to be genetically identical human thymidine phosphorylase in recent years [Nature, 356, 668 (1992)]. Thymidine phosphorylase is an enzyme essential for the metabolism of thymidine, and its development in various tissues (livers, lungs, small intestines, large intestines, placentas, etc.) of human and diverse animals has been confirmed. It has also been reported that in a malignant tumor, its development is promoted in the tumored part compared with its adjacent normal tissue [Biochimica et Biophysica Acta, 1034, 107–113 (1992)] and that this thymidine phosphorylase is also developed very often in clinical samples of human tumors and its development is in a positive correlation with the number of blood vessels in a tumor [Cancer Letters, 95, 57–62 (1995)]. As is appreciated from the foregoing, thymidine phosphorylase/PD-ECGF is considered to have close connection with angiogenesis associated with the growth of a tumor. For the induction of angiogenesis by thymidine phosphorylase, its enzymatic activity has been proven to be indispensable, thereby indicating the possibility of suppression of angiogenesis by inhibiting the enzymatic activity [Cancer Research, 55, 1687–1690 (1995)]. Reported as thymidine phosphorylase inhibitors to date include 6-amino-5-bromo-uracil and 6-aminothimine [Biochemical Pharmacology, 29, 1059 (1980)], 6-amino-5-chlorouracil and 3-cyano-2,6-dihydroxypyridine [JP Kokai 63-250324], and acyclothymidine [J P Kokai 5-213761]. Their inhibitory effects are however not sufficient, and it is the current circumstances that no metastasis inhibitor has been found yet for the suppression of angiogenesis induced by thymidine phosphorylase.

Accordingly, an object of the present invention is to provide a cancerous metastasis inhibitor having excellent inhibitory activity against thymidine phosphorylase.

DISCLOSURE OF THE INVENTION

With the foregoing circumstances in view, the present inventors have proceeded with an investigation from various viewpoints about pharmacological effects of uracil derivatives of a specific type which have heretofore been known to have neither angiogenesis inhibiting effects nor cancererous metastasis inhibiting effects. As a result, these compounds have been found to have extremely good thymidine phosphorylase inhibiting activity and, based on this activity, angiogenesis and cancerous metastasis inhibiting activities, leading to the completion of the present invention.

Accordingly, the present invention relates to a cancerous metastasis inhibitor comprising, as an active ingredient, a uracil derivative represented by the following formula (1):

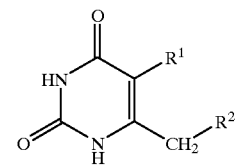

wherein $R^1$ represents a chlorine, bromine or iodine atom or a cyano or lower alkyl group; and $R^2$ represents a 4–8 membered heterocyclic group having 1–3 nitrogen atoms, which may be substituted by one or more lower alkyl, imino, hydroxyl, hydroxymethyl, methanesulfonyloxy, amino or nitro groups; an amidinothio group, one or more of the hydrogen atom(s) on one or both of the nitrogen atoms of which may each be substituted by a lower alkyl group; a guanidino group, one or more of the hydrogen atom(s) on one, two or all of the nitrogen atoms of which may each be substituted by a lower alkyl or cyano group; a (lower alkyl)amidino group; an amino group, one or both of the hydrogen atoms on the nitrogen atom of which may each be substituted by a lower alkyl group; a group —CH$_2$N(R$^a$)R$^b$ in which R$^a$ and R$^b$ may be the same or different and each represents a hydrogen atom or a lower alkyl group or R$^a$ and R$^b$ may form a pyrrolidine ring together with the nitrogen atom to which R$^a$ and R$^b$ are bonded; a group —NH—(CH$_2$)$_m$—Z in which Z represents an amino group, one or both of the hydrogen atoms on the nitrogen atom of which may each be substituted by a lower alkyl group, or a cyano group, and m stands for an integer of from 0 to 3; a group NR$^c$(CH$_2$)$_n$—OH in which R$^c$ represents a hydrogen atom or a lower alkyl group, and n stands for a natural number of from 1 to 4; a group —X—Y in which X represents S or NH, and Y represents a 2-imidazolin-2-yl, 2-imidazolyl, 1-methylimidazol-2-yl, 1,2,4-triazol-3-yl, 2-pyrimidyl or 2-benzimidazolyl group which may be substituted by one or more lower alkyl groups; or a ureido or thioureido group, one or more of the hydrogen atom(s) on one or both of the nitrogen atoms of which may each be substituted by a lower alkyl group; or a salt thereof.

The present invention is also concerned with a cancerous metastasis inhibitor composition comprising the uracil derivative (1) or the salt thereof and a pharmaceutically acceptable carrier.

Further, the present invention pertains to use of the uracil derivative (1) or the salt thereof for the production of a cancerous metastasis inhibitor.

The present invention also relates to a method for the inhibition of metastasis of a cancer, which comprises administering to a patient an effective amount of the uracil derivative (1) or the salt thereof.

BEST MODE FOR CARRYING OUT THE INVENTION

Illustrative of the lower alkyl group represented by R$^1$ and R$^2$ in the formula (1) are linear or branched alkyl groups having 1 to 4 carbon atoms. Specific examples include methyl, ethyl, n-propyl, i-propyl, n-butyl, i-butyl, sec-butyl and t-butyl groups. Among these, a methyl group is particularly preferred.

Illustrative of the 4–8 membered heterocyclic group containing 1–3 nitrogen atoms and represented by R$^2$ are 1-azetidinyl, 1-pyrrolidinyl, 2-pyrrolin-1-yl, 3-pyrrolin-1-yl, 1-pyrrolyl, 1-pyrazolidinyl, 2-pyrazolin-1-yl 3-pyrazolin-1-yl, 4-pyrazolin-1-yl, 1-pyrazolyl, 1-imidazolidinyl, 2-imidazolin-1-yl, 3-imidazolin-1-yl, 4-imidazolin-1-yl, 1-imidazolyl, 1,2,3-triazol-1-yl, 1,2,4-triazol-1-yl, piperidino, 1-piperazyl, morpholino, 1-perhydroazepinyl and 1-perhydroazocinyl groups. Further, these heterocyclic groups may contain one or two substituent groups on their rings. Examples of such substituent groups include lower alkyl, imino, hydroxyl, hydroxymethyl, methanesulfonyloxy, amino and nitro groups. Specific examples of the heterocyclic group which may contain such substituent groups include 1-azetidinyl, 1-pyrrolidinyl, 2,5-dimethylpyrrolidin-1-yl, 2-imino-pyrrolidin-1-yl, 3-hydroxypyrrolidin-1-yl, 2-hydroxy-methylpyrrolidin-1-yl, 3-methanesulfonyloxypyrrolidin-1-yl, 3-aminopyrrolidin-1-yl, 2-pyrrolin-1-yl, 3-pyrrolin-1-yl, 2-imino-3-pyrrolin-1-yl, 1-pyrrolyl, 1-pyrazolidinyl, 2-methylpyrazolidin-1-yl, 4-imino-pyrazolidin-1-yl, 2-pyrazolin-1-yl, 3-pyrazolin-1-yl, 2-methyl-3-pyrazolin-1-yl, 5-imino-3-pyrazolin-1-yl, 4-pyrazolin-1-yl, 2-methyl-4-pyrazolin-1-yl, 3-imino-4-pyrazolin-1-yl, 1-pyrazolyl, 1-imidazolidinyl, 3-methylimidazolidin-1-yl, 2-iminoimidazolidin-1-yl, 2-imino-3-methylimidazolidin-1-yl, 2-imino-3-ethylimidazolidin-1-yl, 2-imino-3-isopropylimidazolidin-1-yl, 2-imidazolin-1-yl, 3-imidazolin-1-yl, 4-imidazolin-1-yl, 3-methyl-4-imidazolin-1-yl, 2-imino-4-imidazolin-1-yl, 2-imino-3-methyl-4-imidazolin-1-yl, 2-imino-3-ethyl-4-imidazolin-1-yl, 2-imino-3-isopropyl-4-imidazolin-1-yl, 1-imidazolyl, 2-methylimidazol-1-yl, 2-nitroimidazol-1-yl, 4-nitroimidazol-1-yl, 1,2,3-triazol-1-yl, 1,2,4-triazol-1-yl, 3-nitro-1,2,4-triazol-1-yl, piperidino, 1-piperazyl, 4-methyl-piperazin-1-yl, morpholino, 1-perhydroazepinyl and 1-perhydroazocinyl groups. Preferred examples include 1-azetidinyl, 1-pyrrolidinyl, 2-iminopyrrolidin-1-yl, 2-iminoimidazolidin-1-yl, 2-imino-3-methylimidazolidin-1-yl, 2-imino-3-ethylimidazolidin-1-yl, 2-imino-3-isopropylimidazolidin-1-yl, 2-imidazolin-1-yl, 2-imino-3-methyl-4-imidazolin-1-yl, 2-imino-3-ethyl-4-imidazolin-1-yl and 1-imidazolyl groups.

Illustrative of the amidinothio group represented by R$^2$, one or more of the hydrogen atom(s) on one or both of the nitrogen atoms of which may each be substituted by a lower alkyl group, are those in which one to three of the three hydrogen atoms on the nitrogen atoms of an amidino group may be substituted by the above lower alkyl group or groups. Especially, amidinothio, N$^1$-methylamidinothio and N$^1$,N$^2$-dimethyl-amidinothio groups are preferred.

Illustrative of the guanidino group, one or more of the hydrogen atom(s) on one, two or all of the nitrogen atoms of which may each be substituted by a lower alkyl or cyano group, are those in each of which one to four of the four hydrogen atoms in a guanidino group may be substituted by the above lower alkyl or cyano group or groups. Especially, 1-guanidino, 1-methylguanidino, 3-methylguanidino, 2,3-dimethyl-guanidino and 2-cyano-3-methylguanidino groups are preferred.

Illustrative of the (lower alkyl)amidino group are those formed of amidino groups and the lower alkyl groups bonded thereto, respectively. Of these, an acetoamidino group is preferred.

Illustrative of the amino group, one or both of the hydrogen atoms on the nitrogen atom of which may each be substituted by a lower alkyl group, are those in each of which one or two of the two hydrogen atoms on an amino group may be substituted by the above lower alkyl group or groups. Of these, amino, N-methylamino, N,N-dimethylamino, N-ethylamino, N,N-diethylamino, N-propylamino and N-isopropylamino groups are preferred.

Preferred examples of the group represented by —CH$_2$N(R$^a$)R$^b$ include N-methylaminomethyl, N,N-dimethyl-aminomethyl and 1-pyrrolidinylmethyl groups.

Preferred examples of the group represented by —NH—(CH$_2$)$_m$—Z include N,N-dimethylhydrazino, N-(2-aminoethyl)amino, N-(2-(N,N-dimethyl)aminoethyl)amino, N-(3-aminopropyl)amino and N-(2-cyanoethyl)amino groups.

Preferred examples of the group NR$^c$(CH$_2$)$_n$—OH include N-(2-hydroxyethyl)-N-methylamino, N-(3-hydroxypropyl)amino and N-(4-hydroxybutyl)amino groups.

Preferred examples of the group represented by —X—Y include 2-imidazolin-2-thio, 2-imidazolin-2-amino, imidazol-2-thio, 1-methylimidazol-2-thio, 1,2,4-triazol-3-thio, pyrimidin-2-thio and benzimidazol-2-thio groups.

Preferred examples of the ureido or thioureido group, one or more of the hydrogen atom(s) on one or both of the nitrogen atoms of which may each be substituted by a lower alkyl group, include ureido and 3-methylthioureido groups.

Preferred examples of the group represented by R$^2$ in the formula (1) include 4–8 membered heterocyclic groups having 1–3 nitrogen atoms, which may each be substituted by one or more lower alkyl, imino, hydroxyl, hydroxymethyl, methanesulfonyloxy, amino or nitro groups; amidinothio groups, one or more of the hydrogen atom(s) on one or both of the nitrogen atoms of each of which may each be substituted by a lower alkyl group; guanidino groups, one or more of the hydrogen atom(s) on one, two or all of the nitrogen atoms of each of which may each be substituted by a lower alkyl or cyano group; or (lower alkyl)amidino groups.

Among the groups represented by $R^2$, preferred specific examples include 1-azetidinyl, 1-pyrrolidinyl, 2-iminopyrrolidin-1-yl, 2-iminoimidazolidin-1-yl, 2-imino-3-methylimidazolidin-1-yl, 2-imino-3-ethyl-imidazolidin-1-yl, 2-imino-3-isopropylimidazolidin-1-yl, 2-imidazolin-1-yl, 2-imino-3-methyl-4-imidazolin-1-yl, 2-imino-3-ethyl-4-imidazolin-1-yl, 1-imidazolyl, amidinothio, $N^1$-methylamidinothio, $N^1,N^2$-dimethyl-amidinothio, 1-guanidino, 1-methylguanidino, 3-methylguanidino, 2,3-dimethylguanidino and acetoamidino groups.

Preferred examples of the uracil derivative represented by the formula (1) include those containing 5-bromo-6-(1-pyrrolidinylmethyl)uracil,
5-chloro-6-(1-azetidinylmethyl)uracil,
5-chloro-6-(1-(2-iminopyrrolidinyl)methyl)uracil hydrochloride,
5-bromo-6-(1-(2-iminopyrrolidinyl)methyl)uracil hydrochloride,
5-cyano-6-(1-(2-iminopyrrolidinyl)methyl)uracil,
5-chloro-6-(1-(2-iminoimidazolidinyl)methyl) uracil,
5-bromo-6-(1-(2-iminoimidazolidinyl)methyl) uracil,
5-chloro-6-(1-imidazolylmethyl)uracil hydrochloride,
2-(5-chlorouracil-6-ylmethyl)isothiourea hydrochloride,
2-(5-cyanouracil-6-ylmethyl)isothiourea hydrochloride,
5-chloro-6-(1-guanidino)methyluracil hydrochloride.

The uracil derivative (1) of the present invention can be prepared, for instance, in accordance with the following Processes A to M, using various compounds as raw materials:

[Process A]

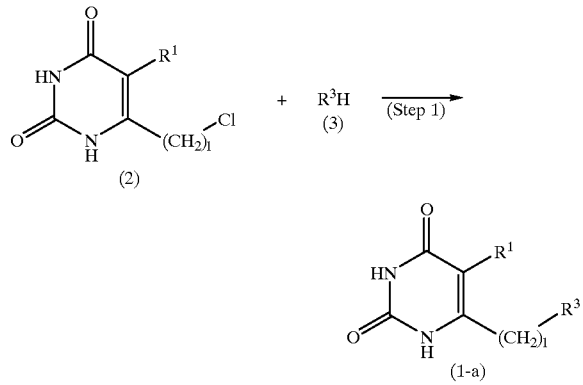

wherein $R^1$ has the same meaning as defined above, 1 a chlorine or bromine atom or a cyano group as $R^1$ and a 1-pyrrolidinyl, 1-azetidinyl, 2-iminopyrrolidin-1-yl, 2-iminoimidazolidin-1-yl, 1-imidazolyl, amidinothio or 1-guanidino group as $R^2$.

Examples of the salt of the uracil derivative (1) can include, but are not particularly limited to, acid-addition salts and/or base salts which have been obtained by causing pharmacologically acceptable acids or basic compounds to act respectively. Examples of these acid addition salts include salts with inorganic acids such as hydrochloric acid, sulfuric acid, phosphoric acid and hydrobromic acid as well as salts with organic acids such as oxalic acid, maleic acid, fumaric acid, malic acid, tartaric acid, citric acid, benzoic acid, acetic acid, p-toluenesulfonic acid and methane-sulfonic acid, with the salt with hydrochloric acid or p-toluenesulfonic acid being preferred. Exemplary base salts include salts with alkali metals and alkaline earth metals such as sodium, potassium, magnesium and calcium as well as salts with amines such as ammonia, methylamine, dimethylamine, piperidine, cyclohexylamine and triethylamine.

Particularly preferred specific examples of the uracil derivative (1) or its salt include:
5-chloro-6-(1-pyrrolidinylmethy)uracil, stands for a number of 1 or 2, and $R^3$ represents a 4–8 membered heterocyclic group having 1–3 nitrogen atoms, which may be substituted by one or more lower alkyl, imino, hydroxyl, hydroxymethyl, amino or nitro groups; a group —NH—$(CH_2)_m$—Z in which Z represents an amino group, one or both of the hydrogen atoms on the nitrogen atom of which may each be substituted by a lower alkyl group, or a cyano group, and m stands for an integer of from 0 to 3; or a group $NR^c(CH_2)_n$—OH in which $R^c$ represents a hydrogen atom or a lower alkyl group, and n stands for a natural number of from 1 to 4.

(Step 1)

The compound represented by the formula (1-a) can be prepared by reacting the compound represented by the formula (2), which is obtained by the below-described preparation processes (Process N) and (Process O), and the known compound represented by the formula (3), which is disclosed in literature [Journal of Organic Chemistry, 32, 738 (1967); Journal of Medicinal Chemistry, 15, 415 (1972)] or is commercially available, in a suitable solvent in the presence or absence of a basic compound.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as diethyl ether, tetrahydrofuran and dioxane; halogenated hydrocarbons such as dichloromethane and chloroform; amines such as pyridine and triethylamine; alkyl ketones such as acetone, methyl ethyl ketone and methyl isobutyl ketone; alcohols such as methanol, ethanol and propanol; and water.

Illustrative basic compounds include organic basic compounds, e.g., tertiary amines such as triethylamine, diisopropylethylamine, tributylamine, pyridine, dimethylaminopyridine and 1,8-diazabicyclo-[5.4.0]undec-7-ene; and inorganic basic compounds, e.g., alkali metal carbonates such as sodium carbonate and potassium carbonate, alkali metal bicarbonates such as sodium bicarbonate and potassium bicarbonate, alkali metal hydroxides such as sodium hydroxide and potassium hydroxide, alkali metals such as sodium and potassium, alkali metal alkoxides such as sodium methoxide, sodium ethoxide and potassium t-butoxide, and alkali metal hydrides such as sodium hydride.

As proportions of the raw materials, it is preferred to use the compound of the formula (3) in an amount of from 1 to 10 mole equivalents, preferably from 1 to 5 mole equivalents and the basic compound in an amount of from 1 to 5 mole equivalents, both per mole of the compound of the formula (2). The reaction temperature may range from 0° C. to the boiling point of the solvent or so, preferably from 0° C. to 80° C. The reaction time may range from 0.1 to 48 hours, preferably from 0.5 to 24 hours.

When $R^3$ is a heterocycle having a hydroxyl group in the compound represented by the formula (1-a), the hydroxyl group can be converted further into a methanesulfonyloxy group by a usual method. Described specifically, the methanesulfonyloxy derivative can be obtained by using N,N-dimethylformamide, dimethylsulfoxide, dichloromethane, pyridine or the like as a solvent, triethylamine, pyridine, dimethylaminopyridine or the like as a basic compound and methanesulfonyl chloride as a mesylating agent, employing the mesylating agent in an amount of from 1 to 2 mole equivalents and the basic compound in an amount of from 1 to 5 mole equivalents, both per mole of the compound of the formula (1-a), and reacting them at a reaction temperate of from 0° C. to the boiling point of the solvent or so for 0.5 to 48 hours.

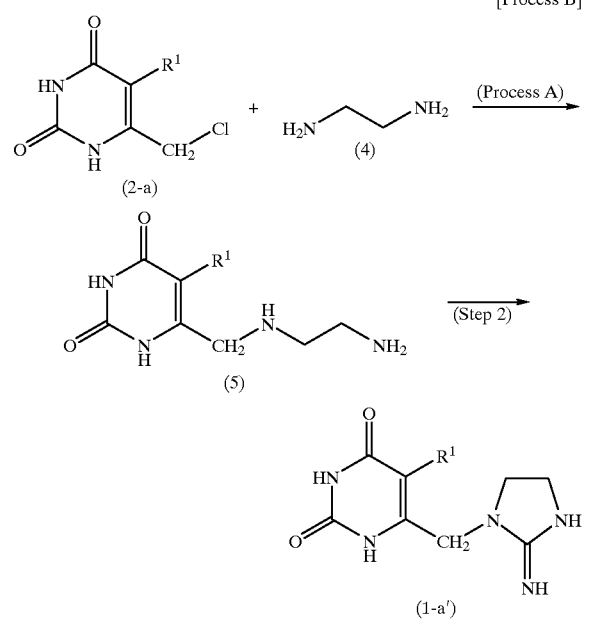

[Process B]

wherein $R^1$ has the same meaning as defined above.

More specifically, the step shown in the above reaction formula can be practiced as will be described hereinafter.

(Step 2)

The compound represented by the formula (1-a') can be prepared by reacting the compound represented by the formula (5), which is obtained by reacting the compound of the formula (2-a) and ethylenediamine (4) in accordance with Process A, with cyanogen bromide in a suitable solvent.

No particular limitation is imposed on the solvent to be used here insofar as it takes no part in the reaction. Examples of the solvent include aprotic polar solvents such as N,N-dimethylformamide, N,N-dimethylacetamide acetonitrile, dimethyl sulfoxide and hexamethylphosphoric triamide; ethers such as diethyl ether, tetrahydrofuran and dioxane; halogenated hydrocarbons such as dichloromethane and chloroform; alcohols such as methanol, ethanol and propanol; and water.

In this reaction, it is preferred to conduct the reaction by using cyanogen bromide in an amount of from 1 to 2 mole equivalents per mole of the compound of the formula (5).

The reaction temperature may range from 0° C. to the boiling point of the solvent or so, preferably from 0° C. to 80° C. The reaction time may range from 0.5 to 48 hours, preferably from 1 to 24 hours.

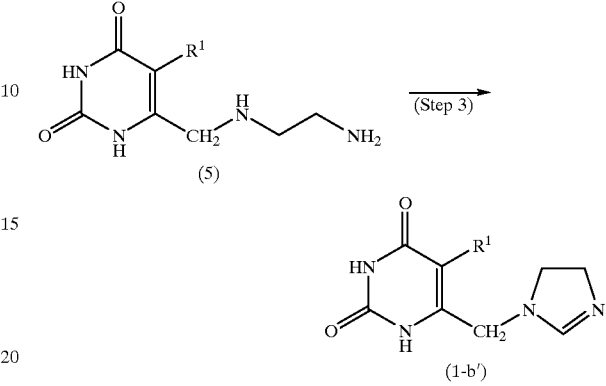

[Process C]

wherein $R^1$ has the same meaning as defined above.

More specifically, the step shown in the above reaction formula can be practiced as will be described hereinafter.

(Step 3)

The compound represented by the formula (1-b') can be prepared by reacting the compound represented by the formula (5) with trimethyl orthoformate in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as diethyl ether, tetrahydrofuran and dioxane; halogenated hydrocarbons such as dichloromethane and chloroform; alcohols such as methanol, ethanol and propanol; and acetic acid, formic acid and water.

In this reaction, it is preferred to use the trimethyl orthoformate in an amount of from 1 to 2 mole equivalents per mole of the compound of the formula (5). The reaction temperature may range from 0° C. to the boiling point of the solvent or so, preferably from 80° C. to 130° C. The reaction time may range from 0.5 to 12 hours, preferably from 1 to 4 hours.

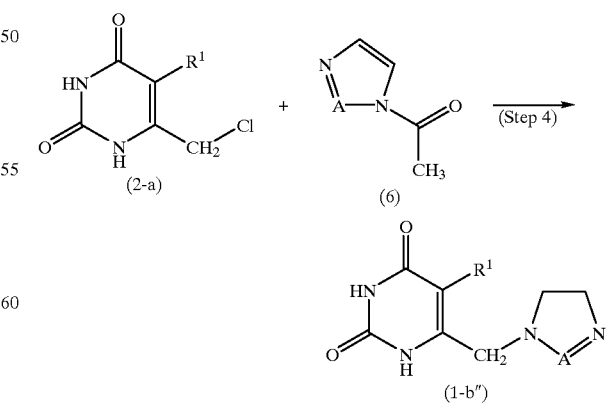

[Process D]

wherein $R^1$ has the same meaning as defined above, and A represents CH or N.

More specifically, the step shown in the above reaction formula can be practiced as will be described hereinafter.
(Step 4)
The compound represented by the formula (1-b") can be prepared by reacting the compound represented by the formula (2-a) with the compound represented by the formula (6) in a suitable solvent.

No particular limitation is imposed on the solvent to be used here insofar as it takes no part in the reaction. Examples of the solvent include aprotic polar solvents such as N,N-dimethylformamide, N,N-dimethylacetamide acetonitrile, dimethyl sulfoxide and hexamethylphosphoric triamide; ethers such as diethyl ether, tetrahydrofuran and dioxane; halogenated hydrocarbons such as dichloromethane and chloroform; alkyl ketones such as acetone, methyl ethyl ketone and methyl isobutyl ketone; alcohols such as methanol, ethanol and propanol; and water.

In this reaction, it is preferred to use the compound of the formula (6) in an amount of from 1 to 2 mole equivalents per mole of the compound of the formula (2-a). The reaction temperature may range from 0° C. to the boiling point of the solvent or so, preferably from 50° C. to 120° C. The reaction time may range from 0.5 to 72 hours, preferably from 1 to 48 hours.

[Process E]

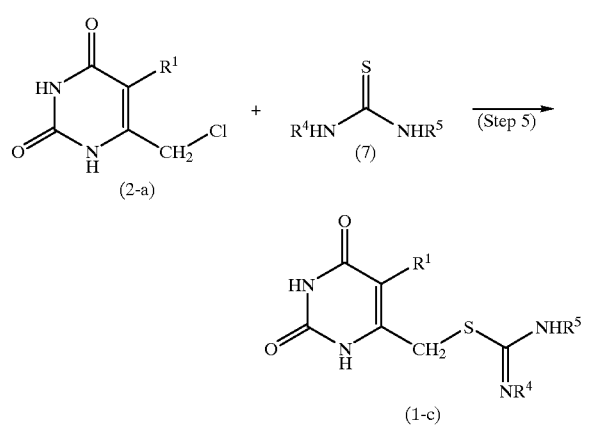

wherein $R^1$ has the same meaning as defined above, and $R^4$ and $R^5$ may be the same or different and each represents a hydrogen atom or a lower alkyl group.

More specifically, the step shown in the above reaction formula can be practiced as will be described hereinafter.
(Step 5)
The compound represented by the formula (1-c) can be prepared by reacting the compound represented by the formula (2-a) with the commercially-available compound represented by the formula (7) in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as diethyl ether, tetrahydrofuran and dioxane; halogenated hydrocarbons such as dichloromethane and chloroform; alkyl ketones such as acetone, methyl ethyl ketone and methyl isobutyl ketone; alcohols such as methanol, ethanol and propanol; and water.

For this reaction, it is preferred to use the compound of the formula (7) in an amount of from 1 to 2 mole equivalents per mole of the compound of the formula (2-a). The reaction temperature may range from 0° C. to the boiling point of the solvent or so, preferably from 50° C. to 120° C. The reaction time may range from 0.5 to 24 hours, preferably from 1 to 8 hours.

[Process F]

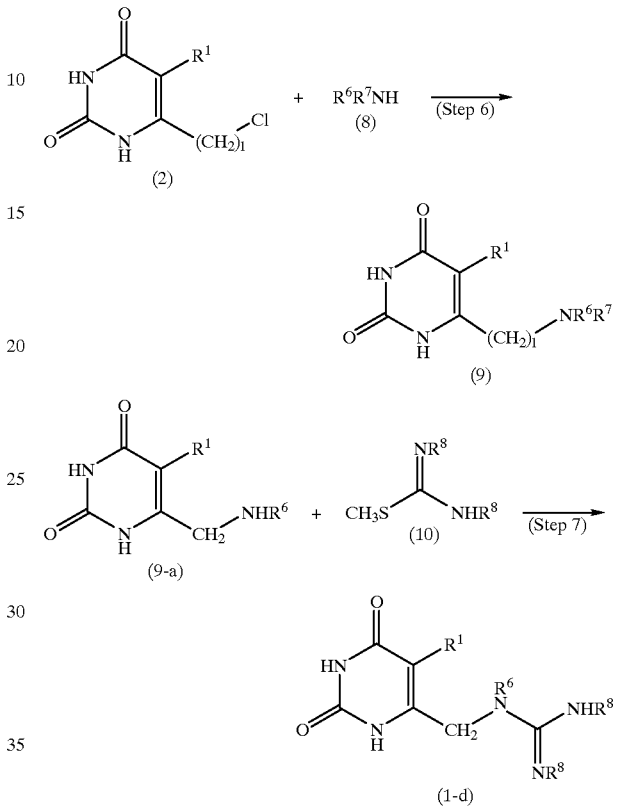

wherein $R^1$ and l have the same meanings as defined above, $R^6$ and $R^7$ may be the same or different and each represents a hydrogen atom or a lower alkyl group, and $R^8$s each represents a hydrogen atom or a lower alkyl group or two $R^8$s represent a 2-imidazolin-2-yl group together with the nitrogen atom to which they are bonded.

More specifically, the individual steps shown in the above reaction scheme can be practiced as will be described hereinafter.
(Step 6)
The compound represented by the formula (9) can be prepared by reacting the compound represented by the formula (2) with the commercially-available compound represented by the formula (8) in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as tetrahydrofuran and dioxane; alcohols such as methanol, ethanol and propanol; and water.

In this reaction, it is preferred to use the compound of the formula (8) in an amount of from 1 to 50 mole equivalents, preferably from 1 to 10 mole equivalents per mole of the compound of the formula (2). The reaction temperature may range from 0° C. to the boiling point of the solvent or so, preferably from 0° C. to 80° C. The reaction time may range from 0.5 to 168 hours, preferably from 1 to 96 hours.

The compound of the formula (9) available by the above reaction can be used in Step 7 with or without isolation.

(Step 7)

The compound represented by the formula (1-d) can be prepared by reacting the compound represented by the formula (9-a) and the known compound represented by the formula (10), which is disclosed in literature [Analytical Biochemistry, 57, 310 (1974)] or is commercially available, in a suitable solvent in the presence or absence of a basic compound.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as tetrahydrofuran and dioxane; alcohols such as methanol, ethanol and propanol; and water.

Illustrative basic compounds include inorganic basic compounds, e.g., alkali metal carbonates such as sodium carbonate and potassium carbonate, alkali metal bicarbonates such as sodium bicarbonate and potassium bicarbonate, alkali metal hydroxides such as sodium hydroxide and potassium hydroxide, alkali metals such as sodium and potassium, alkali metal alkoxides such as sodium methoxide, sodium ethoxide and potassium t-butoxide, and alkali metal hydrides such as sodium hydride.

In this reaction, it is preferred to use the compound of the formula (10) in an amount of from 1 to 2 mole equivalents and the basic compound in an amount of from 1 to 5 mole equivalents, both per mole of the compound of the formula (9-a). The reaction temperature may range from 0° C. to the boiling point of the solvent or so, preferably from 0° C. to 80° C. The reaction time may range from 0.5 to 48 hours, preferably from 1 to 24 hours.

[Process G]

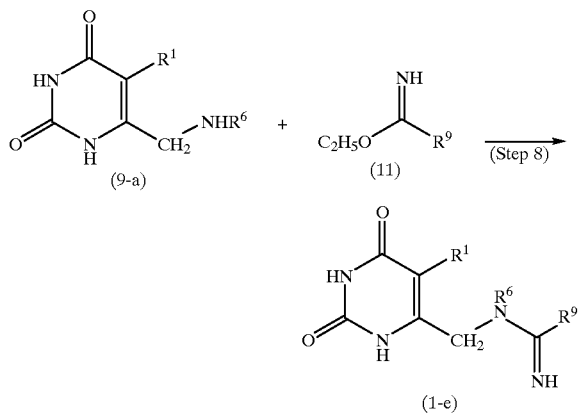

wherein $R^1$ and $R^6$ have the same meanings as defined above, and $R^9$ represents a lower alkyl group.

More specifically, the step shown in the above reaction formula can be practiced as will be described hereinafter.

(Step 8)

The compound represented by the formula (1-e) can be prepared by reacting the compound represented by the formula (9-a) and the compound represented by the formula (11), which is disclosed in literature [Organic Syntheses Collective, 1, 5 (1941)], in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as tetrahydrofuran and dioxane; alcohols such as methanol, ethanol and propanol; and water.

In this reaction, it is preferred to use the compound of the formula (11) in an amount of from 1 to 2 mole equivalents per mole of the compound of the formula (9-a). The reaction temperature may range from 0° C. to the boiling point of the solvent or so, preferably from 0° C. to 80° C. The reaction time may range from 0.5 to 48 hours, preferably from 1 to 24 hours.

[Process H]

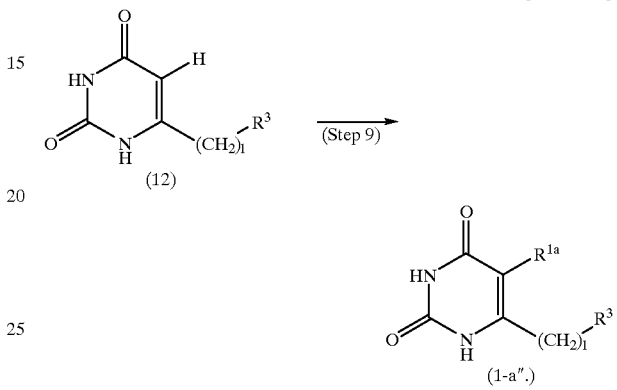

wherein $R^{1a}$ represents a chlorine, bromine or iodine atom, and $R^3$ and l have the same meanings as defined above.

More specifically, the step shown in the above reaction formula can be practiced as will be described hereinafter.

(Step 9)

The compound represented by the formula (1-a") can be prepared by reacting the compound represented by the formula (12), which is obtained in accordance with the below-described preparation process (Process P), with a chlorinating agent, brominating agent or iodating agent in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as tetrahydrofuran and dioxane; alcohols such as methanol, ethanol and propanol; and acetic acid, formic acid, concentrated sulfuric acid and water.

Illustrative of the chlorinating agent are chlorine, N-chlorosuccinimide, sulfuryl chloride and sodium hypochlorite.

Illustrative of the brominating agent are bromine, N-bromosuccinimide and pyridiniumbromide perbromide.

Illustrative of the iodating agent are iodine and N-iodosuccinimide.

In this reaction, it is preferred to use the chlorinating agent, brominating agent or iodating agent in an amount of from 1 to 3 mole equivalents per mole of the compound of the formula (12). The reaction temperature may range from 0° C. to the boiling point of the solvent or so, preferably from 0° C. to 80° C. The reaction time may range from 0.5 to 48 hours, preferably from 1 to 12 hours.

[Process I]

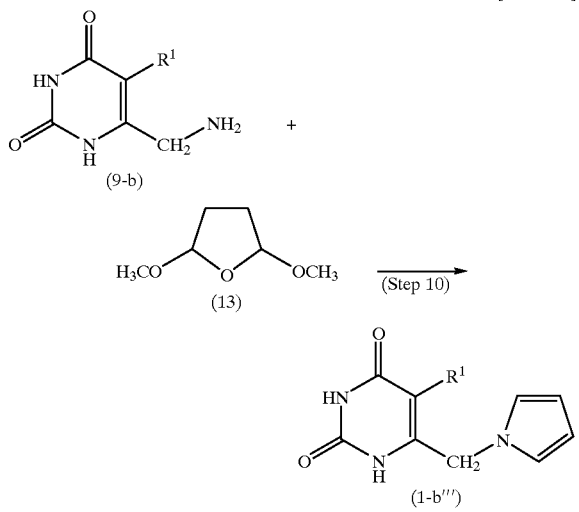

wherein R¹ has the same meaning as defined above.

More specifically, the step shown in the above reaction formula can be practiced as will be described hereinafter.

(Step 10)

The compound represented by the formula (1-b‴) can be prepared by reacting the compound represented by the formula (9-b) and 2,5-dimethoxytetrahydrofuran (13) in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as diethyl ether, tetrahydrofuran and dioxane; alcohols such as methanol, ethanol and propanol; and acetic acid, formic acid, concentrated sulfuric acid and water.

In this reaction, it is preferred to use 2,5-dimethoxytetrahydrofuran (13) in an amount of from 1 to 5 mole equivalents, preferably from 1 to 2 mole equivalents per mole of the compound of the formula (9-b). The reaction temperature may range from 0° C. to the boiling point of the solvent or so, preferably from 0° C. to 120° C. The reaction time may range from 0.5 to 48 hours, preferably from 1 to 24 hours.

[Process J]

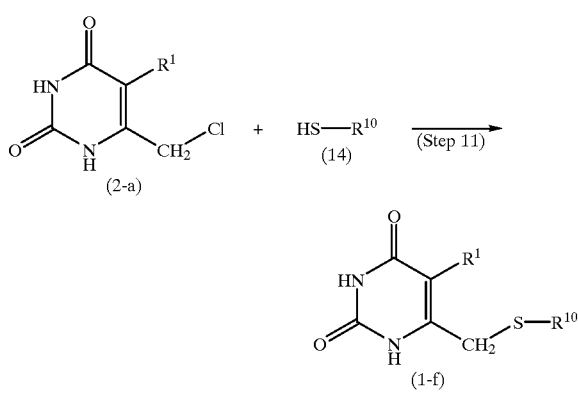

wherein R¹ has the same meaning as defined above, and R¹⁰ represents a 2-imidazolin-2-yl, 2-imidazolyl, 1,2,4-triazol-3-yl, 1-methylimidazol-2-yl, 2-pyrimidyl or 2-benzimidazolyl group.

More specifically, the step shown in the above reaction formula can be practiced as will be described hereinafter.

(Step 11)

The compound represented by the formula (1-f) can be prepared by reacting the compound represented by the formula (2-a) and the commercially-available compound represented by the formula (14) in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as diethyl ether, tetrahydrofuran and dioxane; halogenated hydrocarbons such as dichloromethane and chloroform; alkyl ketones such as acetone, methyl ethyl ketone and methyl isobutyl ketone; alcohols such as methanol, ethanol and propanol; and water.

In this reaction, it is preferred to use the compound of the formula (14) in an amount of from 1 to 3 mole equivalents per mole of the compound of the formula (2-a). The reaction temperature may range from 0° C. to the boiling point of the solvent or so, preferably from 0° C. to 100° C. The reaction time may range from 0.5 to 24 hours, preferably from 1 to 8 hours.

[Process K]

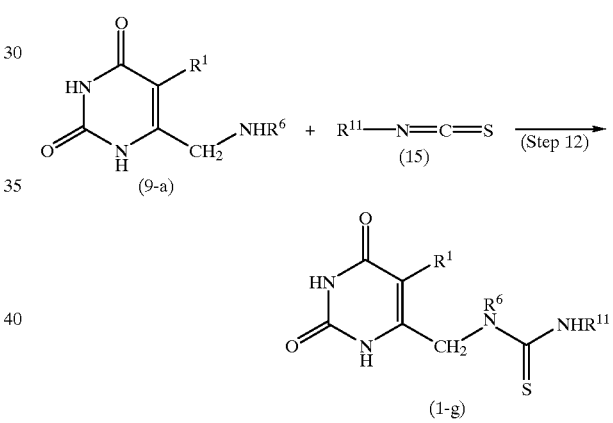

wherein R¹ and R⁶ have the same meanings as defined above, and R¹¹ represents a lower alkyl group.

More specifically, the step shown in the above reaction formula can be practiced as will be described hereinafter.

(Step 12)

The compound represented by the formula (1-g) can be prepared by reacting the compound represented by the formula (9-a) and the compound represented by the formula (15) in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; and ethers such as tetrahydrofuran and dioxane.

In this reaction, it is preferred to use the compound of the formula (15) in an amount of from 1 to 2 mole equivalents per mole of the compound of the formula (9-a). The reaction temperature may range from 0° C. to the boiling point of the solvent or so, preferably from 0° C. to 80° C. The reaction time may range from 0.5 to 48 hours, preferably from 1 to 24 hours.

[Process L]

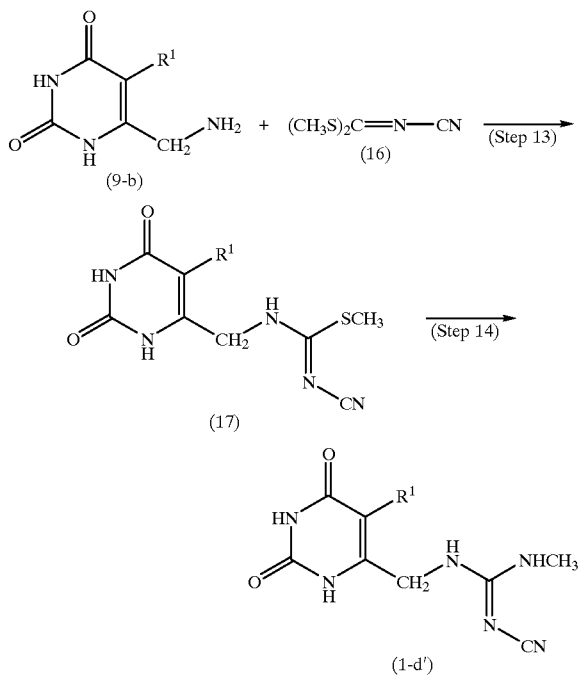

wherein R¹ has the same meaning as defined above.

More specifically, the step shown in the above reaction formula can be practiced as will be described hereinafter.

(Step 13)

The compound represented by the formula (17) can be prepared by reacting the compound represented by the formula (9-b) and S,S'-dimethyl N-cyanodithioiminocarbonate (16), which is a compound commercially available on the market, in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as diethyl ether, tetrahydrofuran and dioxane; halogenated hydrocarbons such as dichloromethane and chloroform; amines such as pyridine and triethylamine; alkyl ketones such as acetone, methyl ethyl ketone and methyl isobutyl ketone; alcohols such as methanol, ethanol and propanol; and water.

In this reaction, it is preferred to use S,S'-dimethyl N-cyanodithioiminocarbonate (16) in an amount of from 1 to 5 mole equivalents, preferably from 1 to 2 mole equivalents per mole of the compound of the formula (9-b). The reaction temperature may range from 0° C. to the boiling point of the solvent or so, preferably from 60° C. to 130° C. The reaction time may range from 0.5 to 24 hours, preferably from 1 to 8 hours.

The compound of the formula (17) available by the above reaction can be used in Step 14 with or without isolation.

(Step 14)

The compound represented by the formula (1-d') can be prepared by reacting the compound represented by the formula (17) and methylamine in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as diethyl ether, tetrahydrofuran and dioxane; halogenated hydrocarbons such as dichloromethane and chloroform; alcohols such as methanol, ethanol and propanol; and water.

In this reaction, it is preferred to use methylamine in an amount of from 1 to 100 mole equivalents per mole of the compound of the formula (17). The reaction temperature may range from 0° C. to the boiling point of the solvent or so, preferably from 0° C. to 80° C. The reaction time may range from 0.5 to 24 hours, preferably from 1 to 8 hours.

[Process M]

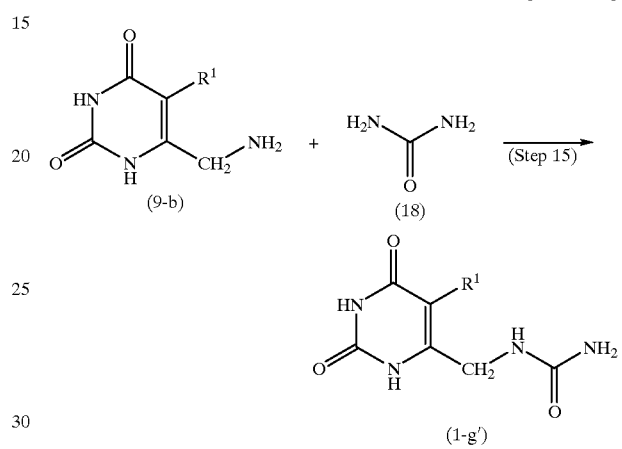

wherein R¹ has the same meaning as defined above.

More specifically, the step shown in the above reaction formula can be practiced as will be described hereinafter.

(Step 15)

The compound represented by the formula (1-g') can be prepared by reacting the compound represented by the formula (9-b) and urea (18) in a suitable solvent.

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as diethyl ether, tetrahydrofuran and dioxane; halogenated hydrocarbons such as dichloromethane and chloroform; amines such as pyridine and triethylamine; alkyl ketones such as acetone, methyl ethyl ketone and methyl isobutyl ketone; alcohols such as methanol, ethanol and propanol; and water.

In this reaction, it is preferred to use urea in an amount of from 1 to 2 mole equivalents per mole of the compound of the formula (9-b). The reaction temperature may range from 0° C. to the boiling point of the solvent or so. The reaction time may range from 0.5 to 48 hours, preferably from 1 to 24 hours.

The compounds represented by the formula (2), which are raw materials for the above-described Process A, Process B, Process D, Process E, Process F and Process J, can be prepared from various compounds as raw materials, for example, in accordance with Process N or Process O which will be described below. On the other hand, 6-chloromethylthymine can be prepared by the process disclosed in literature [Journal of the American Chemical Society, 35, 596 (1913)].

[Process N]

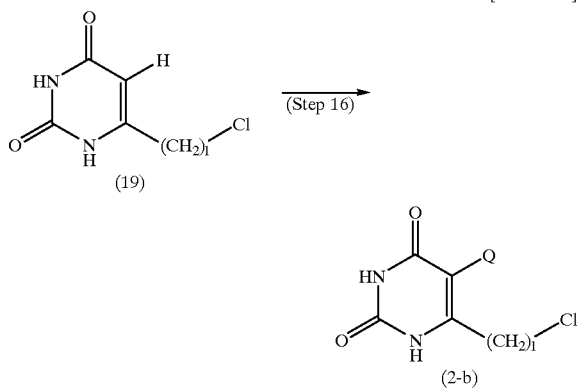

wherein Q represents a chlorine, bromine or iodine atom, and l stands for 1 or 2.

(Step 16)

The compound represented by the formula (2-b) can be prepared following Step 9 of Process H, using as a raw material 6-chloromethyluracil, a commercially-available compound, or 6-(2-chloroethyl)uracil, a compound already known from Journal of Heterocyclic Chemistry, 16, 239 (1979).

[Process O]

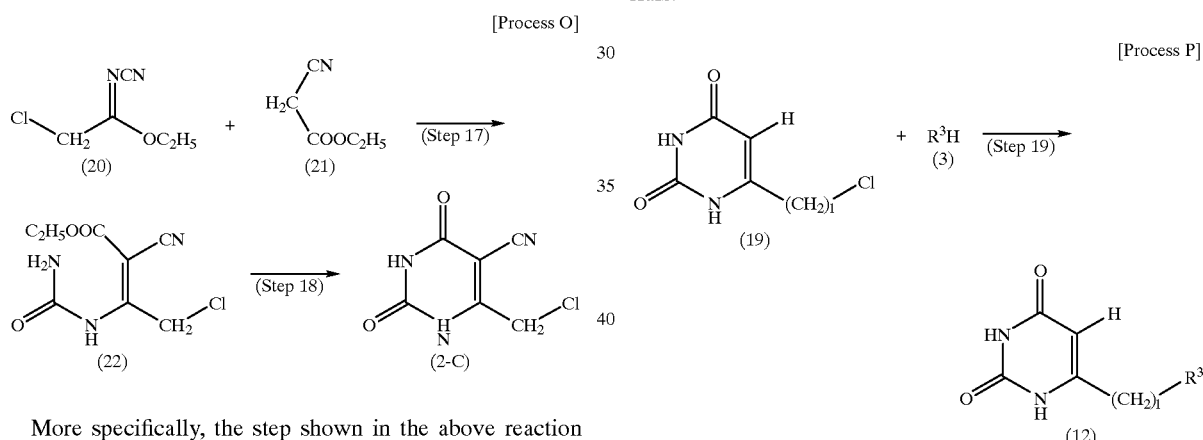

More specifically, the step shown in the above reaction formula can be practiced as will be described hereinafter.

(Step 17)

The compound (22) can be prepared by reacting ethyl 2-chloro-N-cyanoacetoimidate (20) disclosed in literature [Journal of Organic Chemistry, 28, 1816 (1963)] and ethyl cyanoacetate (21) in a suitable solvent in the presence of a basic compound in accordance with the process disclosed in literature [Journal of the Chemical Society Chemical Communications, 350 (1974)].

No particular limitation is imposed on the solvent to be used here insofar as it takes no part in the reaction. Examples of the solvent include aprotic polar solvents such as N,N-dimethylformamide, N,N-dimethylacetamide, acetonitrile, dimethyl sulfoxide and hexamethylphosphoric triamide; ethers such as tetrahydrofuran and dioxane; and alcohols such as methanol, ethanol and propanol.

Illustrative basic compounds include inorganic basic compounds, e.g., alkali metal carbonates such as sodium carbonate and potassium carbonate, alkali metal bicarbonates such as sodium bicarbonate and potassium bicarbonate, alkali metal hydroxides such as sodium hydroxide and potassium hydroxide, alkali metals such as sodium and potassium and alkali metal alkoxides such as sodium methoxide, sodium ethoxide and potassium t-butoxide, and alkali metal hydrides such as sodium hydride.

In this reaction, it is preferred to use ethyl cyanoacetate (21) in an amount of from 1 to 2 mole equivalents and the basic compound in an amount of from 1 to 2 mole equivalents, both per mole of ethyl 2-chloro-N-cyanoacetoimidate (20). The reaction temperature may range from 0° C. to the boiling point of the solvent or so, preferably from 0° C. to 80° C. The reaction time may range from 0.5 to 48 hours, preferably from 1 to 24 hours.

The compound of the formula (22) available by the above reaction can be used in Step 18 with or without isolation.

(Step 18)

The compound (2-c) can be prepared by reacting the compound (22) with sodium hydroxide in water in accordance with the process disclosed in literature [Journal of the Chemical Society Chemical Communications, 350 (1974)].

In the above reaction, it is preferred to use sodium hydroxide in an amount of from 1 to 100 mole equivalents per mole of the compound (22). The reaction temperature may range from 0° C. to the boiling point of the solvent or so, preferably from 0° C. to 50° C. The reaction time may range from 0.5 to 24 hours, preferably from 1 to 6 hours.

Further, the compound according to the present invention represented by the formula (12), which is the raw material for Process H, can be prepared, for example, by the below-described Process P, using various compounds as raw materials.

[Process P]

wherein $R^3$ and l have the same meanings as defined above.

(Step 19)

The compound represented by the formula (12) can be prepared following Step 1 of Process A, using 6-chloromethyluracil or 6-(2-chloroethyl)uracil (19) as a raw material.

The compounds (1) according to the present invention, which have been obtained by Process A, Process B, Process C, Process D, Process E, Process F, Process G, Process H, Process I, Process J, Process K, Process L and Process M, can be used after isolating and purifying them by conventional separation methods, for example, column chromatography, recrystallization, vacuum distillation or the like.

The uracil derivative (1) or its salt according to the present invention, which has been obtained as described above, has excellent human thymidine phosphorylase inhibiting effects and is useful as an effective ingredient for a cancerous metastasis inhibitor.

Incidentally, concerning 5-bromo-4-aminomethyl-uracil of the formula (1) in which $R^1$ is a bromine atom and $R^2$ is an amino group, a synthesis process of its hydrochloride is reported in Acta Poloniae Pharceutica, 27(4), 329 (1970). This report however makes no mention about the inhibitory effects against human-derived thymidine phosphorylase.

Upon administration of the cancerous metastasis inhibitor according to the present invention to mammals including human, it can be formulated into various pharmacological dosage forms depending on the purposes of treatments. Specifically, it can be formulated into oral preparations such as tablets, coated tablets, pills, powders, granules, capsules, solutions, suspensions and emulsions; and parenteral preparations such as injections, suppositories, ointments and plasters. These dosable preparations can each be formulated by a common formulation method generally known in the present field of art while using a pharmaceutically acceptable carrier or the like.

Upon formulation into the form of tablets, usable examples of carriers include excipients such as lactose, sucrose, sodium chloride, glucose, urea, starch, calcium carbonate, kaolin, crystalline cellulose and silicic acid; binders such as water, ethanol, propanol, corn starch, simple syrup, glucose solution, starch solution, gelatin solution, carboxymethyl cellulose, shellac, methyl cellulose, hydroxypropyl cellulose, hydroxypropyl methylcellulose, potassium phosphate and polyvinyl pyrrolidone; disintegrators such as dried starch, sodium alginate, powdered agar, powdered laminarin, sodium bicarbonate, calcium carbonate, polyoxyethylene sorbitan fatty acid esters, sodium lauryl sulfate, stearic acid monoglyceride, starch and lactose; disintegration suppressors such as sucrose, stearic acid, cacao butter and hydrogenated oils; absorbefacients such as quaternary ammonium bases and sodium lauryl sulfate; humectants such as glycerin and starch; adsorbents such as starch, lactose, kaolin, bentonite and colloidal silicic acid; and lubricants such as purified talc, stearate salts, powdered boric acid and polyethylene glycol. Further, tablets may be formed into those applied with conventional coatings as needed, for example, sugar-coated tablets, gelatin-coated tablets, enteric-coated tablets, film-coated tablets, double-layer tablets and multi-layer tablets.

Examples of carriers usable upon formulation into the form of pills include excipients such as glucose, lactose, starch, cacao butter, hydrogenated vegetable oils, kaolin and talc; binders such as powdered gum arabic, powdered tragacanth, gelatin and ethanol; and disintegrators such as laminarin and agar.

Capsules can be formulated by mixing the uracil derivative (1) or its salt with one or more of the above-exemplified various carriers and then filling the resultant mixture in hard gelatin capsules, soft capsules or the like.

To formulate liquid preparations for oral administration, liquid preparation for internal use, syrups and elixirs can be formulated by methods known per se in the art, using taste corrigents, buffers, stabilizers and smell corrigents. Illustrative of the taste corrigents are sucrose, bitter orange peel, citric acid and tartaric acid, illustrative of the buffers is sodium citrate, and illustrative of the stabilizers are tragacanth gum, gum arabic and gelatin.

As a carrier upon formulation into the form of suppositories, it is possible to use, for example, polyethylene glycol, cacao butter, a higher alcohol, an ester of a higher alcohol, gelatin, semisynthetic glyceride or the like.

To formulate injections, it is preferred to sterilize solutions, emulsions or suspensions and to make them isotonic with blood. Usable examples of diluents upon formulation into the form of these injections include water, an aqueous lactic acid solution, ethyl alcohol, propylene glycol, Macrogol, ethoxylated isostearyl alcohol, polyoxylated isostearyl alcohol and polyoxyethylene sorbitan fatty acid esters. In this case, such pharmaceutical preparations may contain sodium chloride, glucose or glycerin in an amount sufficient to prepare isotonic solutions. Further, conventional solubilizing aids, buffers, soothing agents, and the like may also be added.

Examples of diluents usable upon formulation into the form of ointments, for example, pastes, creams and gels include white petrolatum, paraffin, glycerin, cellulose derivatives, polyethylene glycol, silicone and bentonite.

For the formulation of a plaster, it is only necessary to coat a conventional backing material with the above-described ointment, cream, gel, paste or the like by a method known per se in the art. Suitable examples of the backing material include woven fabrics or nonwoven fabrics of cotton, rayon or chemical fibers, and films or foamed sheets of soft PVC, polyethylene or polyurethane.

To the above-described preparations, a coloring matter, a preservative, a perfume, a corrigent, a sweetening and/or the like as well as another pharmaceutical can also be added as needed.

No particular limitations are imposed on the amounts of the uracil derivative (1) or the salt thereof, which are contained in each preparation according to the present invention, and suitable amounts can be chosen as needed. In general, however, it is preferred to control the content of each of them at about 1 to 70 wt. % in each preparation.

No particular limitation is imposed on the administration method for the each preparation according to the present invention. An administration method is determined as desired depending on the form of the preparation, the age, sex and other conditions of the patient, the severity of a symptom of the patient, and the like. For example, oral administration is used for tablets, pills, powders, granules, capsules, solutions, suspensions and emulsions. Injections are intravenously administered either by themselves or as mixtures with a usual fluid replacement such as glucose or amino acids, and if necessary, are also administered by themselves intra-arterially, intramuscularly, intracutaneously, subcutaneously or intraperitoneally. Suppositories are administered intrarectally. Ointments are coated on the skin, the oral mucosa or the like, whereas plasters are applied on the skin.

The dose of the active ingredient in each preparation according to the present invention can be suitably chosen depending on the administration method, the age, sex and other conditions of the patient, the severity of the disease, and the like. As a general standard, the dose of the uracil derivative (1) or the salt thereof may range from about 0.1 to 100 mg/kg/day, preferably from about 0.5 to 50 mg/kg/day. These preparations according to the present invention can each be administered once a day or in about 2 to 4 portions in a day.

Cancerous metastases which can be inhibited by the administration of preparations according to the present invention are not limited to any particular ones but include, for example, liver metastasis, lung metastasis, lymph node metastasis or the like of esophageal carcinoma, gastric cancer, gallbladder and bile duct cancers, pancreas cancer, colon cancer, rectum cancer, head and neck cancers, breast cancer, cervical cancer, ovarian cancer, bladder cancer, prostatic cancer, testis tumor, osteochondroma, skin cancer and the like.

EXAMPLES

The present invention will hereinafter be described more specifically by the following Referential Examples, Examples and Tests but shall not be limited thereto.

Synthesis of the Compound (2-b) by Process N

Referential Example 1

Synthesis of 5-chloro-6-chloromethyluracil

To a suspension of 6-chloromethyluracil (163 g) in acetic acid (500 ml), sulfuryl chloride (120 ml) was added dropwise at room temperature over 20 minutes, followed by stirring at the same temperature for 3 hours. The reaction mixture was poured into ice water (500 ml), and a crystallized matter was collected by filtration, whereby 182.3 g of the title compound were obtained (yield: 92%).

Melting point: 225° C. min. (decomposed).

NMR spectrum (DMSO-$d_6$) δ: 4.46(2H,s), 11.57(1H,s), 11.71(1H,s).

TABLE 1

Elemental analysis (as $C_5H_4N_2O_2Cl_2$)

|  | C | H | N |
|---|---|---|---|
| Calculated | 30.80 | 2.07 | 14.37 |
| Found | 30.85 | 1.99 | 14.41 |

Referential Example 2

Synthesis of 5-bromo-6-chloromethyluracil

A reaction was conducted in a similar manner as Referential Example 1 except that N-bromosuccinimide was used instead of sulfuryl chloride, whereby the title compound was obtained in a yield of 70%.

Melting point: 245° C. min. (decomposed).

NMR spectrum (DMSO-$d_6$) δ: 4.47(2H,s), 11.61(1H,s), 11.66(1H,s).

TABLE 2

Elemental analysis (as $C_5H_4N_2O_2BrCl$)

|  | C | H | N |
|---|---|---|---|
| Calculated | 25.08 | 1.68 | 11.70 |
| Found | 24.81 | 1.67 | 11.57 |

Referential Example 3

Synthesis of 5-iodo-6-chloromethyluracil

A reaction was conducted in a similar manner as Referential Example 1 except that N-iodosuccinimide was used instead of sulfuryl chloride, whereby the title compound was obtained in a yield of 77%.

Melting point: 225° C. min. (decomposed).

NMR spectrum (DMSO-$d_6$) δ: 4.49(2H,s), 11.52(1H,s), 11.58(1H,s).

TABLE 3

Elemental analysis (as $C_5H_4N_2O_2ClI$)

|  | C | H | N |
|---|---|---|---|
| Calculated | 20.96 | 1.41 | 9.78 |
| Found | 21.10 | 1.36 | 9.87 |

Referential Example 4

Synthesis of 5-chloro-6-(2-chloroethyl)uracil

A reaction was conducted in a similar manner as Referential Example 1 except that 6-(2-chloroethyl)uracil was used instead of 6-chloromethyluracil, whereby the title compound was obtained in a yield of 77%.

Melting point: 225° C. min. (decomposed).

NMR spectrum (DMSO-$d_6$) δ: 3.01(2H,t,J=6.9 Hz), 3.88 (2H,t,J=6.9 Hz), 11.28(1H,s), 11.60(1H,s).

TABLE 4

Elemental analysis (as $C_6H_6N_2O_2Cl_2 \cdot 2/5H_2O$)

|  | C | H | N |
|---|---|---|---|
| Calculated | 33.89 | 3.03 | 13.18 |
| Found | 34.27 | 3.02 | 12.75 |

Synthesis of the Compound (2-c) by Process O

Referential Example 5

Synthesis of ethyl 4-chloro-2-cyano-3-ureido-crotonate (22)

A solution of 20 g of ethyl 2-chloro-N-cyanoacetoimidate (20), 16.6 g of ethyl cyanoacetate (21) and 9.28 g of sodium ethoxide in ethanol (350 ml) was stirred at room temperature for 3 hours. After the reaction mixture was distilled, 140 ml of 2 N hydrochloric acid were added, followed by stirring under ice cooling for 1 hour. After the reaction mixture was neutralized with a 2 N aqueous solution of sodium hydroxide, the resultant mixture was extracted with ethyl acetate. The extract was washed with water, dried over anhydrous magnesium sulfate, and then concentrated under reduced pressure. The residue so obtained was purified by chromatography on a silica gel column while using gradient elution with hexane-ethyl acetate, whereby 5.66 g of the title compound were obtained (yield: 18%).

Melting point: 175–177° C.

NMR spectrum (DMSO-$d_6$) δ: 1.27(3H,t,J=6.9 Hz), 4.26 (2H,q,J=6.9 Hz), 5.38(2H,s), 10.05(1H,s).

TABLE 5

Elemental analysis (as $C_8H_{10}N_3O_2Cl$)

|  | C | H | N |
|---|---|---|---|
| Calculated | 41.48 | 4.35 | 18.14 |
| Found | 41.87 | 4.44 | 17.78 |

Referential Example 6

Synthesis of 5-cyano-6-chloromethyluracil (2-b)

Dissolved in 17 ml of a 2 N aqueous solution of sodium hydroxide were 3.88 g of the ethyl 4-chloro-2-cyano-ureidocrotonate (22) obtained in Referential Example 5. The resulting mixture was stirred at room temperature for 1 hour and under ice cooling, was neutralized with 2 N hydrochloric acid. A crystallized matter was collected by filtration, whereby 1.16 g of the title compound were obtained (yield: 37%).

Melting point: 229° C. min. (decomposed).

NMR spectrum (DMSO-$d_6$) δ: 4.45(2H,s), 10.05 (1H,s).

TABLE 6

| Elemental analysis (as $C_6H_4N_3O_2Cl \cdot 1/10H_2O$) | | | |
|---|---|---|---|
| | C | H | N |
| Calculated | 38.46 | 2.26 | 22.43 |
| Found | 38.72 | 2.20 | 22.07 |

Synthesis of the Compound (12) by Process P

Referential Example 7

Synthesis of 6-(1-pyrrolidinylmethyl)uracil

To a solution of 1.78 g of pyrrolidine in water (20 ml), 1.33 g of 6-chloromethyluracil were added. The resulting mixture was stirred at room temperature for 24 hours and neutralized with acetic acid. The reaction mixture was then concentrated under reduced pressure. The residue so obtained was washed with methanol and then filtered, whereby 466 mg of the title compound were obtained (yield: 29%).

Melting point: 176–178° C.

NMR spectrum (DMSO-$d_6$) δ: 1.68–1.76(4H,m), 2.42–2.55(4H,m), 3.49(2H,s), 5.44(1H,s), 10.90(2H,br-s).

TABLE 7

| Elemental analysis (as $C_9H_{13}N_3O_2 \cdot 4/5H_2O$) | | | |
|---|---|---|---|
| | C | H | N |
| Calculated | 51.57 | 7.02 | 20.04 |
| Found | 51.59 | 6.94 | 19.73 |

Physical properties of compounds obtained in the following Examples are presented in Table 9 to Table 28.

Synthesis of the compound (1-a) by Process A

Example 1

Synthesis of 5-chloro-6-(1-pyrrolidinylmethyl)uracil (Compound 1)

To a solution of 32.8 g of pyrrolidine in water (300 ml), 30.0 g of the 5-chloro-6-chloromethyluracil obtained in Referential Example 1 were added. After the resultant mixture was stirred at room temperature for 24 hours, an insoluble matter was removed by filtration. The filtrate was concentrated under reduced pressure. The residue so obtained was washed with methanol and collected by filtration, whereby 14.2 g of the title compound were obtained (yield: 40%).

Example 2

Syntheses of Compounds 2 to 21

Compounds 2 to 21, which are shown in Table 9 to Table 11 and Table 19 to Table 21, were synthesized in a similar manner as in Example 1 by using appropriate starting raw materials.

Example 3

Synthesis of 5-chloro-6-(1-(3-methanesulfonyloxy)-pyrrolidinylmethyl)uracil (Compound 22)

To a solution of 702 mg of the 5-chloro-6-(1-(3-hydroxy) pyrrolidinylmethyl)uracil (Compound 8), which had been obtained in Example 2, in pyridine (5 ml), 350 mg of methanesulfonyl chloride were added. After the resultant mixture was stirred at room temperature for 24 hours, the reaction mixture was purified by chromatography on a silica gel column (chloroformmethanol elution), whereby 220 mg of the title compound were obtained (yield: 24%).

Example 4

Synthesis of 5-chloro-6-(3-nitro-1,2,4-triazol-1-yl-methyl)uracil (Compound 23)

To a solution of 0.88 g of 3-nitro-1,2,4-triazole in a 1 N aqueous solution of KOH (10 ml), 0.50 g of 5-chloro-6-chloromethyluracil was added, followed by heating at 80° C. for 2.5 hours under stirring. The reaction mixture was neutralized with 6 N hydrochloric acid. A precipitate was collected by filtration and then washed with water and methanol, whereby 510 mg of the title compound were obtained (yield: 73%).

Example 5

Syntheses of Compounds 24 to 28

Compounds 24 to 28, which are shown in Table 11 to Table 12 and Table 21 to Table 22, were synthesized in a similar manner as in Example 4 by using appropriate starting raw materials.

Example 6

Synthesis of 5-chloro-6-(1-(2-iminopyrrolidinyl)-methyl)uracil hydrochloride (Compound 29)

A solution of 5.0 g of 5-chloro-6-chloromethyluracil, 6.14 g of 2-iminopyrrolidine and 5.24 g of sodium ethoxide in N,N-dimethylformamide (50 ml) was stirred at room temperature for 14 hours. A crystallized matter was collected by filtration and then suspended in 30 ml of water. After the suspension was neutralized with acetic acid and then washed, an insoluble matter was collected by filtration and then dissolved in 60 ml of 1 N hydrochloric acid. Activated carbon was added to the resultant solution, followed by filtration. The filtrate was concentrated under reduced pressure, and the residue so obtained was washed with ethanol and collected by filtration, whereby 2.68 g of the title compound were obtained (yield: 38%).

Example 7

Synthesis of 5-chloro-6-(1-(2-iminopyrrolidinyl)-methyl)uracil p-toluenesulfonate (Compound 30)

A reaction was conducted in a similar manner as in Example 6 except that p-toluenesulfonic acid was used instead of 1 N hydrochloric acid, whereby the title compound was obtained in a yield of 26%.

Example 8

Syntheses of Compounds 31 to 36

Compounds 31 to 36, which are shown in Table 12 and Table 22, were synthesized in a similar manner as in Example 6 by using appropriate starting raw materials.

Example 9

Synthesis of 6-N-(2-aminoethyl)aminomethyl-5-chlorouracil (Compound 37)

To a solution of 60 g of anhydrous ethylene-diamine in water (200 ml), 39 g of the 5-chloro-6-chloromethyluracil obtained in Referential Example 1 were added. The resulting mixture was stirred at room temperature for 24 hours. A crystallized matter was collected by filtration, whereby 28.35 g of the title compound were obtained (yield: 65%).

Example 10

Synthesis of 6-N-(2-aminoethyl)aminomethyl-5-bromo-uracil (Compound 38)

A reaction was conducted in a similar manner as in Example 9 except that 5-bromo-6-chloromethyluracil was used instead of 5-chloro-6-chloromethyluracil, whereby the title compound was obtained in a yield of 46%.

Example 11

Synthesis of 6-N-(2-aminoethyl)aminomethyl-5-iodo-uracil (Compound 39)

A reaction was conducted in a similar manner as in Example 9 except that 5-iodo-6-chloromethyluracil was used instead of 5-chloro-6-chloromethyluracil, whereby the title compound was obtained in a yield of 69%.

Example 12

Syntheses of Compounds 40 to 43

Compounds 40 to 43, which are shown in Table 13 and Table 23, were synthesized in a similar manner as in Example 9 by using appropriate starting raw materials.

Example 13

Synthesis of 5-chloro-6-(3-hydroxypropylamino) uracil (Compound 44)

To a solution of 580 mg of 3-hydroxypropylamine in water (20 ml), 500 mg of the 5-chloro-6-chloro-methyluracil obtained in Referential Example 1 were added, followed by stirring at room temperature for 19 hours. The reaction mixture was concentrated under reduced pressure and a crude product so obtained was purified by chromatography on a silica gel column (chloroform-methanol-triethylamine elution), whereby 70 mg of the title compound were obtained (yield: 12%).

Example 14

Syntheses of Compounds 45 and 46

Compounds 45 and 46, which are shown in Table 13 to Table 14 and Table 23 to Table 24, were synthesized in a similar manner as in Example 13 by using appropriate starting raw materials.

Synthesis of Compound (1-a') by Process B

Example 15

Synthesis of 5-chloro-6-(1-(2-iminoimidazolidinyl)-methyl)uracil (Compound 47)

To a solution of 3.6 g of cyanogen bromide in water (50 ml), 7.0 g of 6-N-(2-aminoethyl)aminomethyl-5-chlorouracil obtained in Example 9 were added, followed by stirring at room temperature for 3.5 hours. A crystallized matter was collected by filtration, washed with N,N-dimethylformamide and then suspended in 50 ml of water. The suspension was neutralized with a 1 N aqueous solution of sodium hydroxide and an insoluble matter was collected by filtration, whereby 2.65 g of the title compound were obtained (yield: 34%).

Example 16

Syntheses of Compounds 48 and 49

Compounds 48 and 49, which are shown in Table 14 and Table 24, were synthesized in a similar manner as in Example 15 by using appropriate starting raw materials.

Synthesis of Compound (1-b) by Process C

Example 17

Synthesis of 5-chloro-6-(2-imidazolin-1-ylmethyl)-uracil hydrochloride (Compound 50)

To a solution of 1.0 g of the 6-N-(2-aminoethyl)-aminomethyl-5-chlorouracil, which had been obtained in Example 9, in acetic acid (3 ml), 0.56 ml of triethyl orthoformate was added, followed by heating for 1 hour under reflux. To the reaction mixture, 0.1 ml of concentrated hydrochloric acid and 2 ml of acetic acid were added. The resultant mixture was then allowed to cool down. A crystallized matter was collected by filtration and then washed with N,N-dimethylformamide, whereby 220 mg of the title compound were obtained (yield: 18%).

Synthesis of Compound (1-b') by Process D

Example 18

Synthesis of 5-chloro-6-(1-imidazolylmethyl)uracil hydrochloride (Compound 51)

To a solution of 4.3 g of N-acetylimidazole in methanol (100 ml), 5.0 g of 5-chloro-6-chloromethyl-uracil were added, followed by heating for 2 days under reflux. After the reaction mixture was allowed to cool down, a crystallized matter was collected by filtration and then washed with a 10% solution of hydrochloric acid in methanol, whereby 4.32 g of the title compound were obtained (yield: 64%).

Example 19

Synthesis of 5-chloro-6-(1,2,3-triazol-1-ylmethyl) uracil (Compound 52)

A reaction was conducted in a similar manner as in Example 18 except that N-acetyl-1,2,3-triazole was used instead of N-acetylimidazole, whereby the title compound was obtained in a yield of 58%.

Synthesis of Compound (1-c) by Process E

Example 20

Synthesis of 2-(5-chlorouracil-6-ylmethyl) isothiourea hydrochloride (Compound 53)

To a solution of 140 mg of thiourea in ethanol (3 ml), 300 mg of 5-chloro-6-chloromethyluracil were added, followed by heating for 6 hours under reflux. After the reaction mixture was allowed to cool down, a crystallized matter was collected by filtration, whereby 337 mg of the title compound were obtained (yield: 81%).

Example 21

Syntheses of Compounds 54 to 58

Compounds 54 to 58, which are shown in Table 14 to Table 15 and Table 24 to Table 25, were synthesized in a similar manner as in Example 20 by using appropriate starting raw materials.

Synthesis of Compound (9) by Process F

Example 22

Synthesis of 6-aminomethyl-5-chlorouracil (Compound 59)

To 400 ml of a 25% aqueous solution of ammonia, 10 g of the 5-chloro-6-chloromethyluracil obtained in Referential Example 1 were added, followed by stirring at room temperature for 4 days. A crystallized matter was collected by filtration, whereby 7.3 g of the title compound were obtained (yield: 81%).

Example 23

Synthesis of 5-chloro-6-N-methylaminomethyluracil (Compound 60)

To 150 ml of a 40% aqueous solution of methylamine, 6 g of the 5-chloro-6-chloromethyluracil obtained in Referential Example 1 were added. The resulting mixture was stirred at room temperature for 4.5 hours and then concentrated under reduced pressure. The residue so obtained was washed with methanol and then collected by filtration, whereby 5.38 g of the title compound were obtained (yield: 92%).

Example 24

Syntheses of Compounds 61 to 67

Compounds 61 to 67, which are shown in Table 15 to Table 16 and Table 25 to Table 26, were synthesized in a similar manner as in Example 23 by using appropriate starting raw materials.

Synthesis of Compound (1-d) by Process F

Example 25

Synthesis of 5-chloro-6-(1-guanidino)methyluracil hydrochloride (Compound 68)

Subsequent to addition of 455 mg of 2-methyl-isothiourea sulfate to 33 ml of a 0.1 N aqueous solution of potassium hydroxide under ice cooling, 600 mg of the 6-aminomethyl-5-chlorouracil obtained in Example 22 were added, followed by heating for 2 hours at 80° C. under stirring. After the reaction mixture was allowed to cool down, a crystallized matter was collected by filtration and washed with 2 N hydrochloric acid, whereby 287 mg of the title compound were obtained (yield: 33%).

Example 26

Syntheses of Compounds 69 to 72

Compounds 69 to 72, which are shown in Table 16 and Table 26, were synthesized in a similar manner as in Example 25 by using appropriate starting raw materials.

Synthesis of Compound (1-e) by Process G

Example 27

Synthesis of N-(5-chlorouracil-6-ylmethyl)-acetamidine hydrochloride (Compound 73)

To a solution of 705 mg of ethyl acetoimidate hydrochloride in N,N-dimethylformamide (12 ml), 500 mg of 6-aminomethyl-5-chlorouracil were added, followed by stirring at room temperature for 13 hours. After the reaction mixture was allowed to cool down, a crystallized matter was collected by filtration and then washed with a 10% solution of hydrochloric acid in methanol, whereby 190 mg of the title compound were obtained (yield: 26%).

Synthesis of Compound (1-a") by Process H

Example 28

Synthesis of 5-bromo-6-(1-pyrrolidinylmethyl)uracil (Compound 2)

To a solution of 1.0 g of the 6-(1-pyrrolidinylmethyl) uracil, which had been obtained in Referential Example 7, in acetic acid (10 ml), 1.0 g of bromine was added dropwise, followed by stirring at room temperature for 20 hours. A crystallized matter was collected by filtration and then washed with methanol, whereby 560 mg of the title compound were obtained (yield: 40%). The melting point and NMR spectrum of the thus-obtained compound were in full conformity with those of Compound 2 synthesized by Process A in Example 2.

TABLE 8

| Elemental analysis (as $C_9H_{12}N_3O_2Br$) | | | |
|---|---|---|---|
| | C | H | N |
| Calculated | 39.44 | 4.41 | 15.33 |
| Found | 39.48 | 4.47 | 15.43 |

Synthesis of Compound (1-b'") by Process I

Example 29

Synthesis of 5-chloro-(1-pyrrolylmethyl)uracil (Compound 74)

To a solution of 500 mg of the 6-aminomethyl-5-chlorouracil, which had been obtained in Example 22, in acetic acid (8 ml), 577 mg of 2,5-dimethoxytetrahydrofuran were added, followed by heating at 110° C. for 2 hours under stirring. The temperature of the reaction mixture was cooled back to room temperature. After an insoluble matter was filtered off, the filtrate was concentrated under reduced pressure. The residue so obtained was purified by chromatography on a silica gel column (chloroform-methanol elution), whereby 155 mg of the title compound were obtained (yield: 24%).

Synthesis of Compound (1-f) by Process J

Example 30

Synthesis of 5-chloro-6-(2-imidazolylthiomethyl) uracil (Compound 75)

A reaction was conducted in a similar manner as in Example 20 except that 2-mercaptoimidazole was used instead of thiourea, whereby the title compound was obtained in a yield of 77%.

Example 31

Syntheses of Compounds 76 to 80

Compounds 76 to 80, which are shown in Table 17 to Table 18 and Table 27 to Table 28, were synthesized in a similar manner as Example 30 by using appropriate starting raw materials.

Synthesis of Compound (1-g) by Process K

Example 32

Synthesis of N-methyl-N'-(5-chlorouracil-6-ylmethyl)thiourea (Compound 81)

A suspension of 0.50 g of 5-chloro-6-chloromethyluracil and 0.22 g of methyl isothiocyanate in N,N-dimethylformamide (3 ml) was heated at 70° C. for 4 hours under stirring. Water (50 ml) was added to the reaction mixture. A crystallized matter was collected by filtration and then washed with water and methanol, whereby 435 mg of the title compound were obtained (yield: 61%).

Synthesis of Compound (1-d') by Process L

Example 33

Synthesis of N-cyano-N'-methyl-N''-(5-chlorouracil-6-ylmethyl)guanidine (Compound 82)

A suspension of 1.0 g of the 6-aminomethyl-5-chlorouracil obtained in Example 22 and 0.926 g of S,S'-dimethyl-N-cyanodithioiminocarbonate in N,N-dimethylformamide (20 ml) was heated at 120° C. for 3.5 hours under stirring. The reaction mixture was concentrated under reduced pressure. Methanol was added to the residue, followed by filtration. The filtrate was concentrated under reduced pressure. The residue was purified by chromatography on a silica gel column (chloroform-methanol elution), whereby 190 mg of N-cyano-N'-(5-chlorouracil-6-ylmethyl)-S-methylisothiourea were obtained.

Next, 150 mg of the N-cyano-N'-(5-chlorouracil-6-ylmethyl)-S-methylisothiourea were suspended in ethanol (3 ml), followed by the addition of 2 ml of a 30% solution of methylamine in ethanol. The resulting mixture was heated at 50° C. for 3.5 hours under stirring. After an insoluble matter was filtered off, the filtrate was allowed to cool back to room temperature. A precipitate from the filtrate was collected by filtration, whereby 12 mg of the title compound were obtained (yield: 9%).

Synthesis of Compound (1-g') by Process M

Example 34

Synthesis of 5-chloro-6-(ureidomethyl)uracil (Compound 83)

6-Aminomethyl-5-chlorouracil (300 mg) obtained in Example 22 was suspended in 2 N hydrochloric acid (10 ml), followed by concentration under reduced pressure. To the residue, 188 mg of urea and 15 ml of water were added, followed by heating for 24 hours under reflux. After an insoluble matter was filtered off, the filtrate was allowed to cool back to room temperature. A precipitate was collected by filtration and then recrystallized from water, whereby 33 mg of the title compound were obtained (yield: 9%).

TABLE 9

| Compound No. | $R^1$ | $R^2$ | Melting point (° C.) Molecular formula | Yield (%) | Elemental analysis data (%) Calculated (Found) C | H | N |
|---|---|---|---|---|---|---|---|
| 1 | Cl | —N(pyrrolidinyl) | 207–209 $C_9H_{12}N_3O_2Cl$ | 40 | 47.07 (46.97 | 5.27 5.36 | 18.30 18.15) |
| 2 | Br | —N(pyrrolidinyl) | 213–215 $C_9H_{12}N_3O_2Br$ | 60 | 39.44 (39.54 | 4.41 4.44 | 15.33 15.49) |
| 3 | I | —N(pyrrolidinyl) | ≧178 (decomp'd) $C_9H_{12}N_3O_2I$ | 17 | 33.66 (33.73 | 3.77 3.89 | 13.09 13.05) |
| 4 | CN | —N(pyrrolidinyl) | ≧205 (decomp'd) $C_{10}H_{12}N_4O_2$ $H_2O$ | 17 | 50.41 (50.70 | 5.92 5.57 | 23.52 23.29) |
| 5 | $CH_3$ | —N(pyrrolidinyl) | 196–198 $C_{10}H_{15}N_3O_2$ ⅓$H_2O$ | 25 | 56.43 (56.39 | 7.29 7.36 | 19.74 19.62) |

TABLE 9-continued

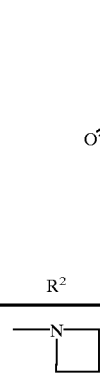

| Compound No. | R$^1$ | R$^2$ | Melting point (° C.) Molecular formula | Yield (%) | Elemental analysis data (%) Calculated (Found) | | |
|---|---|---|---|---|---|---|---|
| | | | | | C | H | N |
| 6 | Cl | 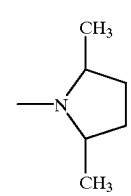 | 190–191 C$_8$H$_{10}$N$_3$O$_2$Cl | 40 | 44.56 (44.34 | 4.67 4.72 | 19.49 19.35) |
| 7 | Cl | 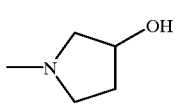 | ≧220 (decomp'd) C$_{11}$H$_{16}$N$_3$O$_2$Cl | 9 | 51.27 (51.13 | 6.26 6.41 | 16.30 16.34) |
| 8 | Cl | 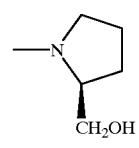 | ≧190 (decomp'd) C$_9$H$_{12}$N$_3$O$_3$Cl | 22 | 44.00 (44.06 | 4.92 5.08 | 17.10 16.94) |
| 9 | Cl | 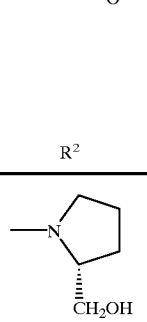 | 165–167 C$_{10}$H$_{14}$N$_3$O$_3$Cl | 53 | 46.25 (46.23 | 5.43 5.60 | 16.18 15.99) |

TABLE 10

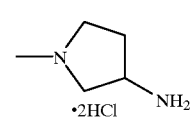

| Compound No. | R$^1$ | R$^2$ | Melting point (° C.) Molecular formula | Yield (%) | Elemental analysis data (%) Calculated (Found) | | |
|---|---|---|---|---|---|---|---|
| | | | | | C | H | N |
| 10 | Cl | | 165–167 C$_{10}$H$_{14}$N$_3$O$_3$Cl | 22 | 46.25 (46.46 | 5.43 5.65 | 16.18 16.10) |
| 11 | Cl | | ≧220 (decomp'd) C$_9$H$_{13}$N$_4$O$_2$Cl 2HCl ⅓H$_2$O | 91 | 33.65 (33.65 | 4.83 4.93 | 17.44 17.41) |

TABLE 10-continued

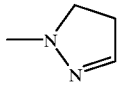

| Compound | | | Melting point (° C.) | Yield | Elemental analysis data (%) Calculated (Found) | | |
|---|---|---|---|---|---|---|---|
| No. | $R^1$ | $R^2$ | Molecular formula | (%) | C | H | N |
| 12 | Cl | 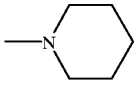 | 233–236<br>$C_8H_9N_4O_2Cl$ | 99 | 42.03<br>(41.72 | 3.97<br>3.86 | 24.50<br>24.10) |
| 13 | Cl | 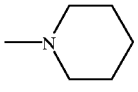 | ≧195 (decomp'd)<br>$C_{10}H_{14}N_3O_2Cl$ | 61 | 49.29<br>(49.37 | 5.79<br>5.83 | 17.24<br>17.15) |
| 14 | Br | 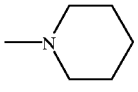 | ≧215 (decomp'd)<br>$C_{10}H_{14}N_3O_2Br$ | 30 | 41.68<br>(41.70 | 4.90<br>5.00 | 14.58<br>14.54) |
| 15 | Cl | 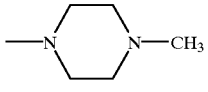 | ≧205 (decomp'd)<br>$C_{10}H_{15}N_4O_2Cl$ | 1 | 46.43<br>(46.44 | 5.84<br>6.05 | 21.66<br>21.53) |
| 16 | Cl | 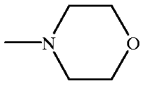 | 245<br>$C_9H_{12}N_3O_3Cl$<br>$\frac{1}{10}H_2O$ | 78 | 43.68<br>(43.68 | 4.97<br>4.81 | 16.98<br>16.89) |
| 17 | Cl | 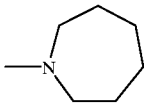 | ≧200 (decomp'd)<br>$C_{11}H_{16}N_3O_2Cl$ | 47 | 51.27<br>(51.39 | 6.26<br>6.50 | 16.30<br>16.37) |
| 18 | Cl | 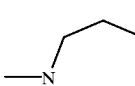 | ≧175 (decomp'd)<br>$C_{12}H_{18}N_3O_2Cl$ | 46 | 53.04<br>(53.03 | 6.68<br>7.03 | 15.46<br>15.39) |

TABLE 11

(structure: uracil with R¹ at 5-position and CH₂R² at 6-position)

| Compound No. | R¹ | R² | Melting point (° C.) Molecular formula | Yield (%) | Calculated (Found) C | H | N |
|---|---|---|---|---|---|---|---|
| 19 | Cl | —CH₂—N(pyrrolidine) | ≧270 (decomp'd) C₁₀H₁₄N₃O₂Cl | 14 | 49.29 (49.00 | 5.79 6.02 | 17.24 16.90) |
| 20 | Cl | 1-methyl-2-(methylamino)imidazol-yl·HCl | ≧250 (decomp'd) C₉H₁₀N₅O₂Cl ¼H₂O | 24 | 36.44 (36.41 | 3.91 3.86 | 23.61 23.55) |
| 21 | Cl | 1-methyl-2-(ethylamino)imidazol-yl·HCl | ≧235 (decomp'd) C₁₀H₁₂N₅O₂Cl H₂O | 7 | 37.05 (37.33 | 4.66 4.33 | 21.60 21.52) |
| 22 | Cl | 1-methyl-3-(methanesulfonyloxy)pyrrolidin-yl | ≧175 (decomp'd) C₁₀H₁₄N₃O₅SCl | 47 | 37.10 (36.93 | 4.36 4.40 | 12.98 12.80) |
| 23 | Cl | 1-methyl-3-nitro-1,2,4-triazol-5-yl | ≧230 (decomp'd) C₇H₅N₆O₄Cl | 73 | 30.84 (30.34 | 1.85 1.76 | 30.83 31.12) |
| 24 | Cl | 1-methylpyrazol-yl | ≧220 (decomp'd) C₈H₇N₄O₂Cl | 17 | 42.40 (42.01 | 3.11 3.05 | 24.72 24.39) |
| 25 | Cl | 1-methyl-2-methylimidazol-yl·HCl | ≧240 (decomp'd) C₉H₉N₄O₂Cl HCl ⅝H₂O | 8 | 36.08 (36.03 | 4.20 3.94 | 18.71 18.44) |
| 26 | Cl | 1-methyl-2-nitroimidazol-yl | ≧185 (decomp'd) C₈H₆N₅O₄Cl | 50 | 35.38 (35.27 | 2.23 2.22 | 25.78 25.68) |
| 27 | Cl | 1-methyl-4-nitroimidazol-yl | 155–158 C₈H₆N₅O₄Cl ⅝H₂O | 12 | 32.67 (32.87 | 2.91 2.73 | 23.81 23.60) |

TABLE 12

[Structure: pyrimidine-2,4-dione with R¹ at 5-position and CH₂R² at 6-position]

| Compound No. | R¹ | R² | Melting point (° C.) Molecular formula | Yield (%) | Elemental analysis data (%) Calculated (Found) C | H | N |
|---|---|---|---|---|---|---|---|
| 28 | Cl | [1,2,4-triazol-1-yl, N-methyl] | ≧235 (decomp'd) $C_7H_6N_5O_2Cl$ ⅓$H_2O$ | 14 | 36.36 (36.74 | 2.79 2.71 | 30.29 29.96) |
| 29 | Cl | [1-methyl-2-iminopyrrolidinyl] HN·HCl | ≧255 (decomp'd) $C_9H_{11}N_4O_2Cl$ HCl ¹⁄₁₀$H_2O$ | 38 | 38.48 (38.32 | 4.38 4.35 | 19.94 19.68) |
| 30 | Cl | [1-methyl-2-iminopyrrolidinyl] HN·TsOH | ≧210 (decomp'd) $C_9H_{11}N_4O_2Cl$ TsOH¹⁄₁₀$H_2O$ | 26 | 46.12 (45.71 | 4.64 4.59 | 13.45 13.89) |
| 31 | Br | [1-methyl-2-iminopyrrolidinyl] HN·HCl | ≧180 (decomp'd) $C_9H_{11}N_4O_2Br$ HCl ⅝$H_2O$ | 13 | 31.23 (31.23 | 4.22 4.31 | 16.19 16.16) |
| 32 | $CH_3$ | [1-methyl-2-iminopyrrolidinyl] HN·HCl | ≧250 (decomp'd) $C_{10}H_{14}N_4O_2$ HCl ½$H_2O$ | 45 | 44.86 (44.55 | 6.02 6.14 | 20.93 20.72) |
| 33 | CN | [1-methyl-2-iminopyrrolidinyl] HN | ≧263 (decomp'd) $C_{10}H_{11}N_5O_2$ ¼$H_2O$ | 29 | 50.52 (50.56 | 4.88 4.70 | 29.46 29.25) |
| 34 | Cl | [1-methyl-3-methyl-2-iminoimidazolidinyl] | ≧215 (decomp'd) $C_9H_{12}N_5O_2Cl$ | 22 | 41.95 (41.64 | 4.69 4.75 | 27.18 26.80) |
| 35 | Cl | [1-methyl-3-ethyl-2-iminoimidazolidinyl] | ≧205 (decomp'd) $C_{10}H_{14}N_5O_2Cl$ ⅙$H_2O$ | 11 | 43.72 (43.69 | 5.26 5.23 | 25.49 25.51) |
| 36 | Cl | [1-methyl-3-isopropyl-2-iminoimidazolidinyl] | ≧220 (decomp'd) $C_{11}H_{16}N_5O_2Cl$ ⅘$H_2O$ | 15 | 44.02 (44.07 | 5.91 5.90 | 23.33 23.37) |

TABLE 13

Structure: pyrimidine-2,4-dione with R¹ at 5-position and CH₂R² at 6-position

| Compound No. | R¹ | R² | Melting point (° C.) Molecular formula | Yield (%) | Calculated (Found) C | H | N |
|---|---|---|---|---|---|---|---|
| 37 | Cl | —NH(CH₂)₂NH₂ | ≧140 (decomp'd) C₇H₁₁N₄O₂Cl ⅓H₂O | 70 | 37.43 (37.44 | 5.23 5.47 | 24.94 24.94) |
| 38 | Br | —NH(CH₂)₂NH₂ | ≧168 (decomp'd) C₇H₁₁N₄O₂Br | 46 | 31.96 (31.73 | 4.21 4.31 | 21.30 21.32) |
| 39 | I | —NH(CH₂)₂NH₂ | ≧145 (decomp'd) C₇H₁₁N₄O₂I | 69 | 27.11 (27.01 | 3.58 3.70 | 18.07 17.91) |
| 40 | Cl | —NH—N(CH₃)₂·HCl | ≧160 (decomp'd) C₇H₁₂N₄O₂Cl₂ | 94 | 32.96 (32.83 | 4.74 4.92 | 21.96 21.93) |
| 41 | Cl | —NH(CH₂)₂N(CH₃)₂ | ≧160 (decomp'd) C₉H₁₅N₄O₂Cl ½HCl ½H₂O | 23 | 32.92 (32.90 | 5.98 6.05 | 17.06 17.14) |
| 42 | Cl | —NH(CH₂)₃NH₂ | ≧135 (decomp'd) C₈H₁₃N₄O₂Cl ⅒H₂O | 6 | 40.98 (40.99 | 5.67 5.89 | 23.89 23.56) |
| 43 | Cl | —NH(CH₂)₂CN | ≧205 (decomp'd) C₈H₉N₄O₂Cl | 89 | 42.03 (42.05 | 3.97 3.89 | 24.50 24.35) |
| 44 | Cl | —NH(CH₂)₃OH | 167–169 C₈H₁₂N₃O₃Cl | 12 | 41.12 (41.12 | 5.18 5.43 | 17.98 18.05) |
| 45 | Cl | —N(CH₃)(CH₂)₂OH | 159–160 C₈H₁₂N₃O₃Cl | 38 | 41.12 (41.17 | 5.19 5.35 | 17.98 17.93) |

TABLE 14

Structure: pyrimidine-2,4-dione with R¹ at 5-position and CH₂R² at 6-position

| Compound No. | R¹ | R² | Melting point (° C.) Molecular formula | Yield (%) | Calculated (Found) C | H | N |
|---|---|---|---|---|---|---|---|
| 46 | Cl | —NH(CH₂)₄OH | 164–166 C₉H₁₄N₃O₃Cl | 2 | 43.64 (43.57 | 5.70 5.92 | 16.97 16.72) |
| 47 | Cl | 2-imino-imidazolidin-1-yl | ≧228 (decomp'd) C₈H₁₀N₅O₂Cl ⅘H₂O | 34 | 36.10 (36.10 | 4.73 4.67 | 26.31 26.24) |
| 48 | Br | 2-imino-imidazolidin-1-yl | ≧235 (decomp'd) C₈H₁₀N₅O₂Br ⅘H₂O | 25 | 30.93 (31.05 | 4.06 3.96 | 22.55 22.70) |

TABLE 14-continued

[Structure: pyrimidine-2,4-dione with R¹ at 5-position and CH₂R² at 6-position]

| Compound No. | R¹ | R² | Melting point (° C.) Molecular formula | Yield (%) | Elemental analysis data (%) Calculated (Found) C | H | N |
|---|---|---|---|---|---|---|---|
| 49 | I | 1-methyl-2-iminoimidazolidin-1-yl | ≧207 (decomp'd) $C_8H_{10}N_5O_2I$ ⅘$H_2O$ | 4 | 27.49 (27.87 | 3.35 3.15 | 20.04 19.54) |
| 50 | Cl | 1-methyl-4,5-dihydroimidazol-1-yl ·HCl | ≧260 (decomp'd) $C_8H_9N_4O_2Cl$ HCl | 18 | 36.38 (36.34 | 3.82 3.83 | 21.21 20.87) |
| 51 | Cl | 1-methylimidazol-1-yl ·HCl | 244–246 $C_8H_7N_4O_2Cl$ HCl ⅔$H_2O$ | 64 | 34.93 (35.14 | 3.42 3.36 | 20.37 20.07) |
| 52 | Cl | 1-methyl-1,2,3-triazol-1-yl | ≧195 (decomp'd) $C_7H_6N_5O_2Cl$ ⅛$H_2O$ | 58 | 36.36 (35.98 | 2.79 2.56 | 30.29 30.63) |
| 53 | Cl | S-methylisothiourea ·HCl | ≧220 (decomp'd) $C_6H_7N_4O_2ClS$ HCl | 81 | 26.58 (26.93 | 2.97 3.05 | 20.66 20.31) |
| 54 | Br | S-methylisothiourea ·HCl | ≧235 (decomp'd) $C_6H_7N_4O_2BrS$ HCl | 23 | 22.84 (22.97 | 2.56 2.68 | 17.75 17.54) |

TABLE 15

[Structure: pyrimidine-2,4-dione with R¹ at 5-position and CH₂R² at 6-position]

| Compound No. | R¹ | R² | Melting point (° C.) Molecular formula | Yield (%) | Elemental analysis data (%) Calculated (Found) C | H | N |
|---|---|---|---|---|---|---|---|
| 55 | $CH_3$ | S-methylisothiourea ·HCl | ≧160 (decomp'd) $C_7H_{10}N_4O_2S$ HCl $H_2O$ | 23 | 31.29 (31.34 | 4.88 5.06 | 20.85 20.90) |

TABLE 15-continued

[Structure: pyrimidine-2,4-dione with R¹ at 5-position and CH₂R² at 6-position]

| Compound No. | R¹ | R² | Melting point (° C.) Molecular formula | Yield (%) | Elemental analysis data (%) Calculated (Found) | | |
|---|---|---|---|---|---|---|---|
| | | | | | C | H | N |
| 56 | CN | —S—C(=NH·HCl)—NH₂ (methyl) | ≥178 (decomp'd) C₇H₇N₅O₂S HCl | 59 | 32.13 (32.33 | 3.08 2.97 | 26.76 26.50) |
| 57 | Cl | —S—C(=NH·HCl)—NHCH₃ (methyl) | ≥205 (decomp'd) C₇H₉N₄O₂ClS HCl | 93 | 29.49 (29.61 | 3.53 3.60 | 19.65 19.70) |
| 58 | Cl | —S—C(=NCH₃·HCl)—NHCH₃ (methyl) | ≥200 (decomp'd) C₈H₁₁N₄O₂ClS HCl | 61 | 32.12 (32.04 | 4.04 4.15 | 18.73 18.54) |
| 59 | Cl | —NH₂ | 210 C₅H₆N₃O₂ ¹/₁₀H₂O | 81 | 33.86 (34.28 | 3.52 3.36 | 23.69 23.20) |
| 60 | Cl | —NHCH₃ | 197–199 C₆H₈N₃O₂Cl | 92 | 38.01 (37.62 | 4.25 4.26 | 22.16 21.94) |
| 61 | Cl | —N(CH₃)₂ | ≥130 (decomp'd) C₇H₁₀N₃O₂Cl | 22 | 41.29 (41.25 | 4.95 5.01 | 20.64 20.42) |
| 62 | Cl | —NHC₂H₅ | 189–191 C₇H₁₀N₃O₂Cl ⅕H₂O | 52 | 40.57 (40.60 | 5.06 5.11 | 20.28 20.05) |
| 63 | Cl | —N(C₂H₅)₂ | ≥155 (decomp'd) C₉H₁₄N₃O₂Cl | 33 | 46.66 (46.39 | 6.09 6.28 | 18.14 17.95) |

TABLE 16

[Structure: pyrimidine-2,4-dione with R¹ at 5-position and CH₂R² at 6-position]

| Compound No. | R¹ | R² | Melting point (° C.) Molecular formula | Yield (%) | Elemental analysis data (%) Calculated (Found) | | |
|---|---|---|---|---|---|---|---|
| | | | | | C | H | N |
| 64 | Cl | —NH(CH₂)₂CH₃ | 193–195 C₈H₁₂N₃O₂Cl ⅕H₂O | 75 | 43.43 (43.60 | 5.65 5.85 | 18.99 18.98) |
| 65 | Cl | —NHCH(CH₃)₂ | ≥185 (decomp'd) C₈H₁₂N₃O₂Cl ¼H₂O | 6 | 43.25 (43.31 | 5.67 5.80 | 18.91 18.86) |
| 66 | Cl | —CH₂NHCH₃ | ≥256 (decomp'd) C₇H₁₀N₃O₂Cl ½H₂O | 21 | 39.54 (39.67 | 5.21 5.21 | 19.76 19.42) |
| 67 | Cl | —CH₂N(CH₃)₂ | ≥263 (decomp'd) C₈H₁₂N₃O₂Cl | 67 | 44.15 (43.83 | 5.56 5.79 | 19.31 18.84) |

TABLE 16-continued

[Structure: pyrimidine-2,4-dione with R¹ at 5-position and CH₂R² at 6-position]

| Compound No. | R¹ | R² | Melting point (° C.) Molecular formula | Yield (%) | Elemental analysis data (%) Calculated (Found) C | H | N |
|---|---|---|---|---|---|---|---|
| 68 | Cl | —NH—C(=NH·HCl)—NH₂ | ≧255 (decomp'd) C₆H₈N₅O₂Cl HCl ¹/₁₀H₂O | 33 | 28.16 (28.37 | 3.62 3.67 | 27.37 27.13) |
| 69 | Cl | —N(CH₃)—C(=NH)—NH₂ | ≧200 (decomp'd) C₇H₁₀N₅O₂Cl H₂O | 22 | 33.68 (33.96 | 4.84 4.97 | 28.05 27.92) |
| 70 | Cl | —NH—C(=NH·HCl)—NHCH₃ | ≧172 (decomp'd) C₇H₁₀N₅O₂Cl HCl H₂O | 42 | 29.65 (29.39 | 4.23 4.58 | 24.17 24.48) |
| 71 | Cl | —N(CH₃)—C(=N·HCl·CH₃)—NHCH₃ | ≧189 (decomp'd) C₈H₁₂N₅O₂Cl HCl H₂O | 12 | 32.01 (32.37 | 5.04 5.26 | 23.33 23.14) |
| 72 | Cl | —NH—(2-imidazolin-2-yl)·HCl | ≧235 (decomp'd) C₈H₁₀N₅O₂Cl HCl ½H₂O | 25 | 33.23 (33.26 | 4.18 4.09 | 24.22 24.13) |

TABLE 17

[Structure: pyrimidine-2,4-dione with R¹ at 5-position and CH₂R² at 6-position]

| Compound No. | R¹ | R² | Melting point (° C.) Molecular formula | Yield (%) | Elemental analysis data (%) Calculated (Found) C | H | N |
|---|---|---|---|---|---|---|---|
| 73 | Cl | —NH—C(=NH·HCl)—CH₃ | ≧220 (decomp'd) C₇H₉N₄O₂Cl HCl ³/₅H₂O | 26 | 31.86 (31.68 | 4.28 4.13 | 21.23 21.49) |
| 74 | Cl | —N(pyrrol-1-yl) | ≧210 (decomp'd) C₉H₈N₃O₂Cl ⅕H₂O | 24 | 47.16 (47.63 | 3.69 3.70 | 18.33 17.92) |

TABLE 17-continued

Structure: pyrimidine-2,4-dione with R¹ at 5-position and CH₂-R² at 6-position

| Compound No. | R¹ | R² | Melting point (°C.) Molecular formula | Yield (%) | Elemental analysis data (%) Calculated (Found) | | |
|---|---|---|---|---|---|---|---|
| | | | | | C | H | N |
| 75 | Cl | —S-(1H-imidazol-2-yl)·HCl | ≧195 (decomp'd) C₈H₇N₄O₂SCl HCl ⅔C₂H₅OH | 77 | 33.71 (33.85 | 3.34 3.45 | 17.87 17.71) |
| 76 | Cl | —S-(4,5-dihydro-1H-imidazol-2-yl)·HCl | ≧220 (decomp'd) C₈H₉N₄O₂SCl HCl | 80 | 32.34 (32.46 | 3.39 3.40 | 18.85 18.98) |
| 77 | Cl | —S-(1-methyl-imidazol-2-yl)·HCl | ≧210 (decomp'd) C₉H₉N₄O₂SCl HCl | 87 | 34.96 (34.90 | 3.26 3.31 | 18.12 17.98) |
| 78 | Cl | —S-(1H-1,2,4-triazol-3-yl)·HCl | ≧215 (decomp'd) C₇H₆N₅O₂SCl HCl | 74 | 28.39 (28.58 | 2.38 2.40 | 23.65 23.49 |
| 79 | Cl | —S-(1H-benzimidazol-2-yl)·HCl | ≧223 (decomp'd) C₁₂H₉N₄O₂SCl HCl | 81 | 41.75 (41.82 | 2.92 2.83 | 16.23 16.20) |

TABLE 18

Structure: pyrimidine-2,4-dione with R¹ at 5-position and CH₂-R² at 6-position

| Compound No. | R¹ | R² | Melting point (°C.) Molecular formula | Yield (%) | Elemental analysis data (%) Calculated (Found) | | |
|---|---|---|---|---|---|---|---|
| | | | | | C | H | N |
| 80 | Cl | —S-(pyrimidin-2-yl) | ≧243 (decomp'd) C₉H₇N₄O₂SCl | 96 | 39.93 (40.01 | 2.61 3.11 | 20.70 20.47) |

TABLE 18-continued

[Structure: pyrimidine-2,4-dione with R¹ at position 5 and CH₂R² at position 6]

| Compound No. | R¹ | R² | Melting point (° C.) Molecular formula | Yield (%) | Elemental analysis data (%) Calculated (Found) C | H | N |
|---|---|---|---|---|---|---|---|
| 81 | Cl | —NH-C(=S)-NHCH₃ | ≧195 (decomp'd) C₇H₉N₄O₂SCl ⅔H₂O | 61 | 32.86 (32.81 | 3.86 3.58 | 21.89 21.83) |
| 82 | Cl | —NH-C(=NCN)-NHCH₃ | ≧145 (decomp'd) C₈H₉N₆O₂Cl | 9 | 37.44 (37.27 | 3.53 3.50 | 32.74 33.03) |
| 83 | Cl | —NH-C(=O)-NH₂ | ≧225 (decomp'd) C₆H₇N₄O₃Cl H₂O | 9 | 30.46 (30.31 | 3.83 3.71 | 23.68 23.04) |

TABLE 19

[Structure: pyrimidine-2,4-dione with R¹ at position 5 and CH₂R² at position 6]

| Compound No. | R¹ | R² | NMR spectrum (DMSO-$d_6$) δ |
|---|---|---|---|
| 1 | Cl | pyrrolidin-1-yl | 1.66–1.76(4H, m), 2.48–2.60(4H, m), 3.52(2H, s) |
| 2 | Br | pyrrolidin-1-yl | 1.64–1.79(4H, m), 2.52–2.63(4H, m), 3.55(2H, s) |
| 3 | I | pyrrolidin-1-yl | 1.64–1.79(4H, m), 2.49–2.57(4H, m), 3.57(2H, s), 11.36(1H, br-s) |
| 4 | CN | pyrrolidin-1-yl | 1.75–1.85(4H, m), 2.80–2.88(4H, m), 3.82(2H, s) |
| 5 | CH₃ | pyrrolidin-1-yl | 1.67–1.75(4H, m), 1.78(3H, s), 2.45–2.55(4H, m), 3.38(2H, s) |

TABLE 19-continued

| Compound No. | R¹ | R² | NMR spectrum (DMSO-d$_6$) δ |
|---|---|---|---|
| 6 | Cl | (azetidinyl) | 1.98(2H, quintet, J = 7.0 Hz), 3.27(4H, t, J = 7.0 Hz), 3.46(2H, s), 11.23(1H, br-s) |
| 7 | Cl | (2,5-dimethylpyrrolidinyl) | 1.00(6H, d, J = 5.9 Hz), 1.38(2H, m), 1.83(2H, m), 2.67(2H, m), 3.59(2H, s) |
| 8 | Cl | (3-hydroxy-1-methylpyrrolidinyl) | 1.56(1H, m), 2.01(1H, m), 2.40–2.50(2H, m), 2.68–2.78(2H, m), 3.55(2H, s), 4.16(1H, m), 4.82(1H, br, s) |
| 9 | Cl | (2-hydroxymethyl-1-methylpyrrolidinyl) | 1.57–1.82(4H, m), 2.30(1H, q, J = 8.0 Hz), 2.65(1H, m), 2.92(1H, m), 3.30(1H, dd, J = 11.3, 4.6 Hz), 3.44(1H, dd, J = 11.3, 3.8 Hz), 3.55(1H, d, J = 5.3 Hz), 3.81(1H, d, J = 5.3 Hz), 4.72(1H, br, s), 11.46(1H, br, s) |

TABLE 20

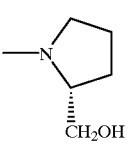

| Compound No. | R¹ | R² | NMR spectrum (DMSO-d$_6$) δ |
|---|---|---|---|
| 10 | Cl | (2-hydroxymethyl-1-methylpyrrolidinyl) | 1.55–1.85(4H, m), 2.30(1H, q, J = 7.8 Hz), 2.65(1H, m), 2.92(1H, m), 3.25–3.37(1H, m), 3.44(1H, dd, J = 11.2, 3.6 Hz), 3.55(1H, d, J = 5.3 Hz), 3.81(1H, d, J = 5.3 Hz), 4.67(1H, br, s), 10.60(1H, br, s), 11.51(1H, br, s) |
| 11 | Cl | (3-amino-1-methylpyrrolidinyl) ·2HCl | (in D$_2$O) 2.14(1H, m), 2.56(1H, m), 3.43–3.68(3H, m), 3.84(1H, dd, J = 8.1, 12.7 Hz), 4.13(1H, m), 4.37(2H, s) |
| 12 | Cl | (pyrazolinyl) | 2.61(2H, d, J = 9.2 Hz), 3.01(2H, d, J = 9.2 Hz), 3.94(2H, s), 6.92(1H, s), 11.49(1H, s), 11.57(1H, s) |

TABLE 20-continued
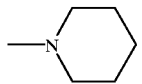
| Compound No. | R¹ | R² | NMR spectrum (DMSO-$d_6$) δ |
|---|---|---|---|
| 13 | Cl | 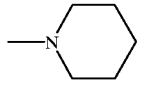 | 1.32–1.56(6H, m), 2.34–2.46(4H, m), 3.36(2H, s), 11.11(1H, br, s) |
| 14 | Br | 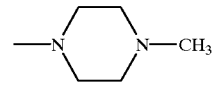 | 1.31–1.58(6H, m), 2.36–2.53(4H, m), 3.37(2H, s), 11.39(1H, br, s) |
| 15 | Cl | 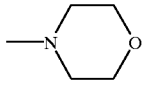 | 2.14(3H, s), 2.25–2.45(4H, br, s), 2.45–2.55(4H, br, s), 3.33(2H, s) |
| 16 | Cl | 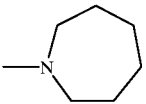 | 2.44–2.47(4H, m), 3.40(2H, s), 3.56–3.60(4H, m), 10.84(1H, br, s), 11.53(1H, br, s) |
| 17 | Cl | 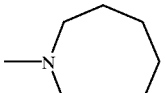 | 1.51–1.66(8H, m), 2.62–2.70(4H, m), 3.54(2H, s) |
| 18 | Cl | 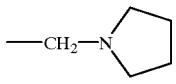 | 1.45–1.63(10H, m), 2.55–2.65(4H, m), 3.49(2H, s) |
TABLE 21
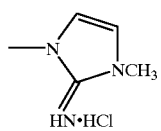
| Compound No. | R¹ | R² | NMR spectrum (DMSO-$d_6$) δ |
|---|---|---|---|
| 19 | Cl | (pyrrolidinylmethyl) | (in CDCl₃) 1.89(4H, quintet, J=3.3Hz), 2.68(4H, t, J=3.3Hz), 2.82(2H, m), 2.93(2H, m), 3.64(2H, s) |
| 20 | Cl | (imidazoline HN·HCl) | 3.46(3H, s), 5.04(2H, s), 7.06(1H, d, J=11.4 Hz), 7.07(1H, d, J=11.4Hz), 8.11(2H, br-s), 11.38(1H, br-s), 11.70(1H, s) |

TABLE 21-continued

Compound of formula with R¹ at 5-position and CH₂R² at 6-position of uracil.

| Compound No. | R¹ | R² | NMR spectrum (DMSO-d₆) δ |
|---|---|---|---|
| 21 | Cl | 1-methyl-3-ethyl-imidazol-2-ylidene·HCl | 1.26(3H, J=7.2Hz), 3.89(2H, q, J=7.2Hz), 5.06(2H, s), 7.07(1H, d, J=2.6Hz), 7.15(1H, d, J=2.6Hz), 8.19(1H, s), 11.47(1H, s), 11.72(1H, s) |
| 22 | Cl | 1-methylpyrrolidin-3-yl methanesulfonate | 1.92(1H, m), 2.26(1H, m), 2.51(1H, m) 2.79–2.94(3H, m), 3.18(3H, s), 3.56(2H, s), 5.15(1H, m), 10.94(1H, br.s), 11.54(1H, br.s) |
| 23 | Cl | 1-methyl-3-nitro-1,2,4-triazol-5-yl | 5.44(2H, s), 8.99(1H, s), 11.55–11.65(1H, br.s), 11.79(1H, br.s) |
| 24 | Cl | 1-methyl-pyrazol-5-yl | 5.17(2H, s), 6.29(1H, dd, J=2.3, 1.5Hz), 7.50(1H, d, J=1.5Hz), 7.86(1H, d, J=2.3 Hz), 11.53(1H, s), 11.68(1H, s) |
| 25 | Cl | 1,2-dimethyl-imidazol-5-yl·HCl | 2.60(3H, s), 5.22(2H, s), 7.54(1H, d, J=2.0Hz), 7.61(1H, d, J=2.0Hz), 11.77(1H, s) |
| 26 | Cl | 1-methyl-2-nitro-imidazol-5-yl | 5.54(2H, s), 7.23(1H, d, J=1.2Hz), 7.68(1H, d, J=1.2Hz), 11.20–11.60(1H, br.s), 11.70(1H, s) |
| 27 | Cl | 1-methyl-4-nitro-imidazol-5-yl | 5.18(2H, s), 7.95(1H, d, J=1.3Hz), 8.43(1H, d, J=1.3Hz), 11.50(1H, s), 11.70(1H, s) |

TABLE 22

| Compound No. | R¹ | R² | NMR spectrum (DMSO-d$_6$) δ |
|---|---|---|---|
| 28 | Cl | 1-methyl-1,2,4-triazol-5-yl | 5.26(2H, s), 8.03(1H, s), 8.64(1H, s), 11.57(1H, s), 11.70(1H, s) |
| 29 | Cl | 1-methyl-2-iminopyrrolidin-2-yl·HCl | 2.04(2H, quintet, J=7.6Hz), 2.87(2H, t, J=7.6Hz), 3.59(2H, t, J=7.6Hz), 4.69(2H, s), 9.40(1H, s), 9.75(1H, s), 11.46(1H, s), 11.73(1H, s) |
| 30 | Cl | 1-methyl-2-iminopyrrolidin-2-yl·TsOH | 2.05(2H, quintet, J=7.7Hz), 2.29(3H, s), 2.87(2H, t, J=7.7Hz), 3.60(2H, t, J=7.7 Hz), 4.56(2H, s), 7.11(2H, d, J=7.3Hz), 7.47(2H, d, J=7.3Hz) 9.51(1H, br-s), 11.0–11.8(2H, very br) |
| 31 | Br | 1-methyl-2-iminopyrrolidin-2-yl·HCl | 2.05(2H, quintet, J=7.4Hz), 2.86(2H, t, J=7.4Hz), 3.59(2H, t, J=7.4Hz), 4.63(2H, s), 9.29(1H, br-s), 9.68(1H, br-s), 11.44(1H, s), 11.69(1H, s) |
| 32 | CH$_3$ | 1-methyl-2-iminopyrrolidin-2-yl·HCl | 1.76(3H, s), 2.02(2H, quintet, J=7.6Hz), 2.84(2H, t, J=7.6Hz), 3.51(2H, t, J=7.6Hz), 4.55(2H, s) |
| 33 | CN | 1-methyl-2-iminopyrrolidin-2-yl | 2.07(2H, quintet, J=7.6Hz), 2.89(2H, t, J=7.6Hz), 3.65(2H, t, J=7.6Hz), 4.50(2H, s), |
| 34 | Cl | 1,3-dimethyl-2-iminoimidazolidin-2-yl | 2.92(3H, s), 3.57(4H, s), 4.27(2H, s) |
| 35 | Cl | 1-methyl-3-ethyl-2-iminoimidazolidin-2-yl | 1.11(3H, t, J=7.3Hz), 3.35(2H, q, J=7.3Hz), 3.59(4H, s), 4.26(2H, s), 9.76(1H, s) |
| 36 | Cl | 1-methyl-3-isopropyl-2-iminoimidazolidin-2-yl | 1.15(6H, d, J=6.3Hz), 3.48–3.62(4H, m), 4.04(1H, septet, J=6.3Hz), 4.26(2H, s) |

TABLE 23

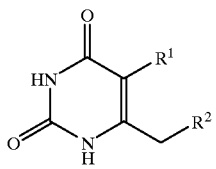

| Compound No. | R¹ | R² | NMR spectrum (DMSO-d$_6$) δ |
|---|---|---|---|
| 37 | Cl | —NH(CH$_2$)$_2$NH$_2$ | 2.57–2.72(4H, m), 3.59(2H, s) |
| 38 | Br | —NH(CH$_2$)$_2$NH$_2$ | 2.63–2.75(4H, m), 3.58(2H, s) |
| 39 | I | —NH(CH$_2$)$_2$NH$_2$ | 2.58–2.72(4H, m), 3.58(2H, s) |
| 40 | Cl | —NH—N(CH$_3$)$_2$·HCl | 3.39(6H, s), 4.67(2H, s), 6.48(2H, s), 11.49(1H, s), 11.84(1H, s) |
| 41 | Cl | —NH(CH$_2$)$_2$N(CH$_3$)$_2$ | 2.83(6H, s), 3.42(4H, s), 4.12(2H, s), 8.42(1H, br.s), 11.76(1H, br.s) |
| 42 | Cl | —NH(CH$_2$)$_3$NH$_2$ | 1.59(2H, quintet, J=6.1Hz), 2.58(2H, t, J=6.1Hz), 2.83(2H, t, J=6.1Hz), 3.55(2H, s) |
| 43 | Cl | —NH(CH$_2$)$_2$CN | 2.61(2H, t, J=6.4Hz), 2.74(2H, t, J=6.4Hz), 3.66(2H, s), 6.66(1H, br.s) |
| 44 | Cl | —NH(CH$_2$)$_3$OH | 1.55(2H, quintet, J=6.6Hz), 2.54(2H, t, J=6.6Hz), 3.44(2H, t, J=6.6Hz), 3.63(2H, s) |
| 45 | Cl | —N(CH$_3$)(CH$_2$)$_2$OH | 2.21(3H, s), 2.49–2.53(2H, m), 3.48(2H, t, J=5.4Hz), 3.52(2H, s), 4.73(1H, br.s), 10.60(1H, br.s), 11.52(1H, br.s) |

TABLE 24

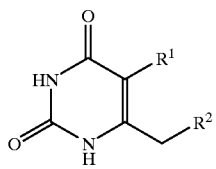

| Compound No. | R¹ | R² | NMR spectrum (DMSO-d$_6$) δ |
|---|---|---|---|
| 46 | Cl | —NH(CH$_2$)$_4$OH | 1.38–1.48(4H, m), 2.46–2.51(2H, m), 3.38(2H, t, J=5.6Hz), 3.63(2H, s) |
| 47 | Cl | 1-methyl-2-imino-imidazolidin-3-yl | 3.45–3.70(4H, s), 4.26(2H, s) |
| 48 | Br | 1-methyl-2-imino-imidazolidin-3-yl | 3.48–3.68(4H, s), 4.25(2H, s) |
| 49 | I | 1-methyl-2-imino-imidazolidin-3-yl | 3.45–3.68(4H, m), 4.22(2H, s) |
| 50 | Cl | 1-methyl-imidazol-3-yl·HCl | 3.78–3.98(4H, m), 4.60(2H, s), 8.59(1H, s), 10.90(1H, br-s), 11.71(1H, s) |

TABLE 24-continued

Structure: 5-R¹, 6-CH₂R² uracil

| Compound No. | R¹ | R² | NMR spectrum (DMSO-d₆) δ |
|---|---|---|---|
| 51 | Cl | 1-methylimidazole·HCl | 5.40(2H, s), 7.74(1H, d, J=1.3 Hz), 7.82(1H, d, J=1.3Hz), 9.29(1H, s), 11.74(1H, s), 11.78(1H, br-s) |
| 52 | Cl | 1-methyl-1,2,3-triazole | 5.45(2H, s), 7.79(1H, s), 8.26(1H, s), 11.69(1H, s), 11.74(1H, s) |
| 53 | Cl | S-methylisothiourea·HCl | 4.35(2H, s), 9.46(4H, br-s), 11.57(1H, br-s), 11.70(1H, br-s) |
| 54 | Br | S-methylisothiourea·HCl | 4.33(2H, s), 9.42(4H, br-s), 11.60(1H, br-s), 11.66(1H, br-s) |

TABLE 25

Structure: 5-R¹, 6-CH₂R² uracil

| Compound No. | R¹ | R² | NMR spectrum (DMSO-d₆) δ |
|---|---|---|---|
| 55 | CH₃ | S-methylisothiourea·HCl | 1.81(3H, s), 4.26(2H, s), 9.39(4H, br-s), 10.83(1H, br-s), 11.18(1H, br-s) |
| 56 | CN | S-methylisothiourea·HCl | 4.33(2H, s) |
| 57 | Cl | N-methyl S-methylisothiourea·HCl | 2.90(3H, s), 4.32(2H, s), 9.40(1H, br-s), 9.77(1H, br-s), 10.20(1H, br-s), 11.51(1H, br-s), 11.67(1H, br-s) |
| 58 | Cl | N,N'-dimethyl S-methylisothiourea·HCl | 2.93(3H, s), 3.03(3H,s), 4.27(2H, s), 9.60(1H, br-s), 9.94(1H, br-s), 11.53(1H, br-s), 11.67(1H, br-s) |
| 59 | Cl | —NH₂ | 3.60(2H, s) |
| 60 | Cl | —NHCH₃ | 2.27(3H, s), 3.61(2H, s) |
| 61 | Cl | —N(CH₃)₂ | 2.22(6H, s), 3.33(2H, s), 11.41(1H, br.s) |

TABLE 25-continued

[Structure: pyrimidine-2,4-dione with R¹ at 5-position and CH₂R² at 6-position]

| Compound No. | R¹ | R² | NMR spectrum (DMSO-$d_6$) δ |
|---|---|---|---|
| 62 | Cl | —NHC₂H₅ | 1.02(3H, t, J=7.1Hz), 2.53(2H, q, J=7.1Hz), 3.64(2H, s) |
| 63 | Cl | —N(C₂H₅)₂ | 0.97(6H, t, J=7.1Hz), 2.55(4H, q, J=7.1Hz), 3.49(2H, s) |

TABLE 26

[Structure: pyrimidine-2,4-dione with R¹ at 5-position and CH₂R² at 6-position]

| Compound No. | R¹ | R² | NMR spectrum (DMSO-$d_6$) δ |
|---|---|---|---|
| 64 | Cl | —NH(CH₂)₂CH₃ | 0.86(3H, t, J=7.3Hz), 1.41(2H, tq, J=7.3, 7.3Hz), 2.44(2H, t, J=7.3Hz), 3.63(2H, s), 8.05(1H, br.s) |
| 65 | Cl | —NHCH(CH₃)₂ | 0.99(6H, d, J=6.1Hz), 2.70(1H, sept, J=6.1Hz), 3.64(2H, s) |
| 66 | Cl | —CH₂NHCH₃ | 2.32(3H, s), 2.67(2H, d, J=6.4Hz), 2.79(2H, d, J=6.4Hz) |
| 67 | Cl | —CH₂N(CH₃)₂ | (in CDCl₃) 2.36(6H, s), 2.71–2.82(4H, m) |
| 68 | Cl | —N(H)—C(=NH·HCl)—NH₂ (N-methyl) | 4.29(2H, d, J=5.0Hz), 7.45(3H, br-s), 7.99(1H, t, J=5.0Hz), 11.45(1H, br-s), 11.64(1H, br-s) |
| 69 | Cl | —N(CH₃)—C(=NH·HCl)—NH₂ | 2.88(3H, s), 4.48(2H, s), 7.65(4H, s), 11.39(1H, br-s), 11.63(1H, br-s) |
| 70 | Cl | —N(H)—C(=NH·HCl)—NHCH₃ | 2.54(3H, d, J=4.6Hz), 4.28(2H, d, J=5.5Hz), 7.57(1H, br-s), 7.74–7.82(2H, m), 11.37(1H, br-s), 11.66(1H, s) |
| 71 | Cl | —N(H)—C(=N·CH₃·HCl)—NHCH₃ | 2.77(6H, d, J=4.6Hz), 4.32(2H, d, J=5.6Hz), 7.66–7.80(3H, m), 11.29(1H, s), 11.67(1H, s) |
| 72 | Cl | —NH—(2-imidazolin-2-yl)·HCl | 3.62(4H, s), 4.38(2H, d, J=5.6Hz), 8.45(1H, br.s), 8.69(1H, t, J=5.6Hz), 11.44(1H, s), 11.67(1H, s) |

TABLE 27

| Compound No. | R¹ | R² | NMR spectrum (DMSO-d₆) δ |
|---|---|---|---|
| 73 | Cl | (H-N-C(CH₃)=NH·HCl) | 2.19(3H, s), 4.40(2H, d, J=5.0Hz), 9.13(1H, s), 9.63(1H, s), 9.86(1H, d, J=5.0Hz), 11.53(1H, s), 11.73(1H, s) |
| 74 | Cl | (N-methylpyrrol-1-yl) | 4.92(2H, s), 6.04(2H, d, J=1.8Hz), 6.87(2H, d, J=1.8Hz), 11.61(2H, br.s) |
| 75 | Cl | (-S-imidazol-2-yl·HCl) | 4.03(2H, s), 7.81(2H, s), 11.30–11.50(1H, br.s), 11.60(1H, s) |
| 76 | Cl | (-S-4,5-dihydroimidazol-2-yl·HCl) | 3.34(4H, s), 4.41(2H, s), 10.50–10.70(1H, br.s), 11.70(1H, s) |
| 77 | Cl | (-S-(1-methylimidazol-2-yl)·HCl) | 3.88(3H, s), 3.99(2H, s), 7.77(1H, d, J=1.7Hz), 7.90(1H, d, J=1.7Hz), 11.41(1H, s), 11.60(1H, s) |
| 78 | Cl | (-S-1,2,4-triazol-3-yl·HCl) | 4.11(2H, s), 8.55(1H, s), 11.33(1H, s), 11.58(1H, s) |
| 79 | Cl | (-S-benzimidazol-2-yl·HCl) | 4.35(2H, s), 7.33–7.63(4H, m), 11.63(1H, s) |

TABLE 28

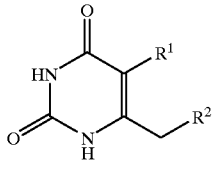

| Compound No. | R¹ | R² | NMR spectrum (DMSO-d$_6$) δ |
|---|---|---|---|
| 80 | Cl | 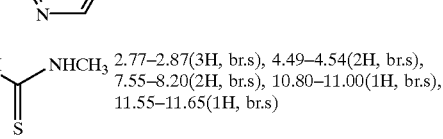 | 4.31(2H, s), 7.30(1H, t, J=5.0Hz), 8.69(2H, d, J=5.0Hz), 11.36(1H, s), 11.61(1H, s) |
| 81 | Cl | —NH-C(=S)-NHCH₃ | 2.77–2.87(3H, br.s), 4.49–4.54(2H, br.s), 7.55–8.20(2H, br.s), 10.80–11.00(1H, br.s), 11.55–11.65(1H, br.s) |
| 82 | Cl | —NH-C(=NCN)-NHCH₃ | 2.72(3H, d, J=3.6Hz), 4.21(2H, d, J=4.6Hz), 7.17–7.35(2H, m), 11.03(1H, s), 11.58(1H, s) |
| 83 | Cl | —NH-C(=O)-NH₂ | 4.09(2H, d, J=5.9Hz), 5.86(2H, s), 6.40(1H, t, J=5.9Hz), 10.70–10.95(1H, br.s), 11.54(1H, s) |

Preparation Example 1 (Tablets)

TABLE 29

| Compound 29 | 25.0 mg |
|---|---|
| Lactose | 8.0 |
| Crystalline cellulose | 4.0 |
| Magnesium stearate | 1.0 |
| Talc | 1.0 |
| Corn starch | 3.5 |
| Hydroxypropyl methylcellulose | 2.5 |
| Tablet | 45.0 mg |

In accordance with the above formula, tablets were prepared in a manner know per se in the art.

Preparation Example 2 (Granules)

TABLE 30

| Compound 29 | 50.0 mg |
|---|---|
| Lactose | 85.0 |
| Corn starch | 100.0 |
| Hydroxypropyl cellulose | 3.0 |
| Granules | 238.0 mg |

In accordance with the above formula, granules were prepared in a manner per se in the art.

Preparation Example 3 (Capsules)

TABLE 31

| Compound 29 | 50.0 mg |
|---|---|
| Lactose | 24.0 |
| Crystalline cellulose | 13.0 |
| Magnesium stearate | 1.0 |
| Capsule | 88.0 mg |

In accordance with the above formula, capsules were prepared in a manner known per se in the art.

Test 1 (Thymidine Phosphorylase Inhibiting Effects)

Inhibitory effects of some uracil derivatives (I) or salts thereof on thymidine phosphorylase were each determined by measuring the formation of [6-³H]thymine from [6-³H] thymidine in the below-described manner.

Namely, reacted at 37° C. for 5 minutes were 0.05 ml of a 3 mM aqueous solution of thymidine (which contained 74 Bq/ml of [6-³H]thymidine), 0.05 ml of a 0.5 M potassium phosphate buffer (pH 7.4), 0.05 ml of a solution of one of the test compounds at one of various concentrations or purified water as a control, and 0.1 ml of a solution of thymidine phosphorylase obtained from human placenta in a highly purified form, 0.25 ml in total. Immediately after the reaction, the reaction mixture was heated for 2 minutes in a boiling water bath of 100° C. to terminate the reaction, followed by centrifugation at 3000 rpm for 10 minutes. Subsequent to the centrifugation, a portion (10 μl) of the resultant supernatant was spotted on a silica gel 60F$_{254}$ plate of 2.0×10 cm and was then dried in air. The plate was placed in a developer bath which was filled with chloroform-methanol-acetic acid (v/v/v, 17:3:1), so that the spot was developed to a position of about 8 cm. The silica gel plate was pulled out and then dried in air. Under a UV lamp, a position ($R_f$ 0.46) of [6-$^3$H]thymine was marked. Silica gel was scraped off from the position by a stainless steel spatula and then placed in a vial for liquid scintillation. One hundred microliters of 2 N HCl were added to moisten the silica gel, whereby [6-$^3$H]thymine was liberated from the gel. Thereafter, 10 ml of scintillator ("AQUASOL-II", product of Amersham International plc) were added, followed by thorough agitation with a stirrer. Radioactivity was then measured by a scintillation counter ("WALLAC SYSTEM 1410", manufactured by Pharmacia AB).

Inhibitory activities of the test compound were determined by the following formula:

$$\text{Inhibition rate } (\%) = \left\{1 - \frac{\text{Amount of } [6-^3H] \text{ thymine in the presence of the test solution } (dpm) - \text{Blank } (dpm)}{\text{Amount of } [6-^3H] \text{ thymine in the control } (dpm) - \text{Blank } (dpm)}\right\} \times 100$$

The concentration of each test solution which inhibited 50% of the amount of [6-$^3$H]thymine formed by thymidine phosphorylase is shown as $IC_{50}$ ($\mu$M) in Table 32.

To compare inhibitory activities, $IC_{50}$s of 6-amino-5-chlorouracil, 6-amino-5-bromouracil, 6-aminothymine, acyclothymidine and 3-cyano-2,6-dihydroxypyrimidine were also measured and calculated.

TABLE 32

| Compound No. or Compound Name | $IC_{50}$ ($\mu$M) |
| --- | --- |
| 1 | 2.2 |
| 2 | 0.51 |
| 3 | 1.3 |
| 6 | 2.6 |
| 20 | 0.24 |
| 29 | 0.035 |
| 32 | 0.12 |
| 33 | 0.017 |
| 34 | 0.046 |
| 47 | 0.013 |
| 48 | 0.030 |
| 50 | 1.2 |
| 51 | 1.0 |
| 53 | 0.35 |
| 56 | 0.10 |
| 57 | 0.15 |
| 68 | 0.27 |
| 73 | 1.5 |
| 6-Amino-5-chlorouracil | 12 |
| 6-Amino-5-bromouracil | 19 |
| 6-Aminothymine | 100 |
| Acyclothymidine | >1000 |
| 3-Cyano-2,6-dihydroxypyridine | 130 |

Test 2 (Effects of Life Prolongation on Liver Metastasis Model)

Effects of life prolongation were assessed using a liver metastasis model system consisting of BALB/c-nu/nu male mice (seven weeks old) each of which had been transplanted in the spleen thereof with 1×10$^6$ cells/mouse of TMK-1 (human gastric cancer) cells.

Specific experimental procedures were carried out by modifying the method proposed by Morikawa et al. in Cancer Research, 48, 1943–1948 (1988). Described specifically, cells which had been cultured in vitro were collected with 0.25%(w/v) trypsin-0.2%(w/v) EDTA and were then washed with a physiological phosphate buffer. The cells were next counted, followed by dilution to 1×10$^6$ cells/50 $\mu$l. Under anesthetization with 30 mg/kg of "Nembutal", each of the mice was incised at its left abdominal region and the spleen was then pulled out. The cell suspension of 10$^6$ cells/50 $\mu$l which had been prepared above was injected in an amount of 50 $\mu$l into the spleen by a syringe fitted with a 28-gauge injection needle. After the mouse was left over for 2 minutes, the blood vessel to the spleen was tied at two positions by ligating clips, respectively, and the spleen was cut off. The excised abdominal region was closed with a suturing stapler. Compound No. 29 of the present invention, in a form dissolved in distilled water, was orally administered everyday for 42 days from the day following the transplant. Using the increase of life span (ILS%) of a control as a reference, an assessment was conducted by observing the mouse for 120 days after the transplant of the cells to confirm its survival. The increase of life span (ILS%) was calculated in accordance with the following formula. The results are presented in Table 33.

$$\text{Increase of life span } (ILS \%) = \left(\frac{\text{Average number of survival time in the drug-administered group}}{\text{Average number of survival time in control}} - 1\right) \times 100$$

Compound No. 29 was found to significantly prolong the period of survival and, compared with the control, prolonged the period of survival by 39.6% in a 50 mg/kg/day administration group and by 43.2% in a 100 mg/kg/day administration group.

TABLE 33

| Group | N | Daily dose (mg/kg/day) | Average # of survival time (days) | ILS (%) |
| --- | --- | --- | --- | --- |
| Control | 9 | — | 63.4 | — |
| Drug-administered | 8 | 50 | 88.5 | 39.6 |
| Drug-administered | 9 | 100 | 90.8 | 43.2 |

Test 3 (Metastasis Inhibiting Effects on Liver Metastasis Model)

About 100 mm$^3$ of human colon cancer strain Co-3 were transplanted to the cecum of each SPF KSN-nu/nu male mouse (seven weeks old). Two weeks after the transplant, a primary carcinoma lesion was removed by surgically cutting off the cecum. On the fourth day after the removal, Compound No. 29 was suspended in a 0.5% (w/v) hydroxypropyl methylcellulose solution (0.5% HPMC solution), an the thus-prepared suspension was orally administered. The administration was conducted for 6 courses, each consisting of administration of 5 straight days followed by a suspension of administration for 2 days. To mice in a control, only 0.5% (w/v) hydroxypropyl methylcellulose solution was orally administered. On the day following the completion of the administration, each mouse was sacrificed and metastasis to the liver was determined based on autopsy. The results are presented in Table 34.

Compared with the control, Compound No. 29 inhibited liver metastasis by 50% in an 18.4 mg/kg/day administration group and by 75% in a 36.9 mg/kg/day administration group.

TABLE 34

| Group | N | Daily dose (mg/kg/day) | Number of metasta- sized mice | Metastasis inhibition rate (%) |
|---|---|---|---|---|
| Control | 6 | — | 4/6 | — |
| Drug-administered | 6 | 18.4 | 2/6 | 50 |
| Drug-administered | 6 | 36.9 | 1/6 | 75 |

Capability of Exploitation in Industry

The uracil derivatives (1) and their salts have the merits that they have extremely great thymidine phosphorylase inhibiting activities compared with conventionally-known thymidine phosphorylase inhibitors and inhibit cancerous metastases extremely well. Accordingly, the cancerous metastasis inhibitors according to the present invention have extremely high utility.

What is claimed is:

1. A method for the treatment of metastasis of a cancer against which a uracil derivative of formula (I) or a salt thereof is effective, comprising administering to a patient in need of such treatment, a therapeutically effective amount of said uracil derivative represented by the formula (I) or said salt thereof:

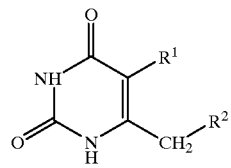

(1)

wherein $R^1$ represents a chlorine, bromine or iodine atom or a cyano or lower alkyl group; and $R^2$ represents a 4–8 membered heterocyclic group having 1–3 nitrogen atoms, which may be substituted by one or more lower alkyl, imino, hydroxyl, hydroxymethyl, methanesulfonyloxy, amino or nitro groups; an amidinothio group, one or more of the hydrogen atoms on one or both of the nitrogen atoms of which may each be substituted by a lower alkyl group; a guanidino group, one or more of the hydrogen atoms on one, two or all of the nitrogen atoms of which may each be substituted by a lower alkyl or cyano group; a lower alkyl amidino group; an amino group, one or both of the hydrogen atoms on the nitrogen atom of which may each be substituted by a lower alkyl group; a group —$CH_2N(R^a)R^b$ in which $R^a$ and $R^b$ may be the same or different and each represents a hydrogen atom or a lower alkyl group or $R^a$ and $R^b$ may form a pyrrolidine ring together with the nitrogen atom to which $R^a$ and $R^b$ are bonded; a group —NH—$(CH_2)_m$—Z in which Z represents an amino group, one or both of the hydrogen atoms on the nitrogen atom of which may each be substituted by a lower alkyl group, or a cyano group, and m stands for an integer of from 0 to 3; a group $NR^c(CH_2)_n$—OH in which $R^C$ represents a hydrogen atom or a lower alkyl group, and n stands for a natural number of from 1 to 4; a group —X—Y in which X represents S or NH, and Y represents a 2-imidazolin-2-yl, 2-imidazolyl, 1-methylimidazol-2-yl, 1,2,4-triazol-3-yl, 2-pyrimidyl or 2-benzimidazolyl group which may be substituted by one or more lower alkyl groups; or a ureido or thioureido group, one or more of the hydrogen atoms on one or both of the nitrogen atoms of which may each be substituted by a lower alkyl group, and wherein the metastasis of a cancer is metastasis to the liver, lung or lymph node by esophageal carcinoma, gastric cancer, gallbladder cancer, bile duct cancer, pancreatic cancer, colon cancer, rectal cancer, head cancer, neck cancer, breast cancer, cervical cancer, ovarian cancer, bladder cancer, prostatic cancer, testis tumor, osteochondroma or skin cancer.

2. The method of treatment according to claim 1, wherein for the uracil derivative of formula (I), the group represented by $R^2$ is a 4–8 membered heterocyclic group having 1–3 nitrogen atoms, and which may be substituted by one or more lower alkyl, imino, hydroxyl, hydroxy-methyl, methanesulfonyloxy, amino or nitro groups; an amidinothio group, one or more of the hydrogen atoms on one or both of the nitrogen atoms of which may each be substituted by a lower alkyl group; a guanidino group, one or more of the hydrogen atoms on one, two or all of the nitrogen atoms of which may each be substituted by a lower alkyl or cyano group; or a lower alkyl amidino group.

3. The method of treatment according to claim 1 or 2, wherein for the uracil derivative of formula (I), the 4–8 membered heterocyclic group represented by $R^2$ and having 1–3 nitrogen atoms is selected from the group consisting of 1-azetidinyl, 1-pyrrolidinyl, 2-pyrrolin-1-yl, 3-pyrrolin-1-yl, 1-pyrrolyl, 1-pyrazolidinyl, 2-pyrazolin-1-yl, 3-pyrazolin-1yl, 4-pyrazolin-1-yl, 1-pyrazolyl, 1-imidazolidinyl, 2-imidazolin-1-yl, 3-imidazolin-1-yl, 4-imidazolin-1-yl, 1-imidazolyl, 1,2,3-triazol-1-yl, 1,2,4-triazol-1-yl, piperidino, 1-piperazyl, morpholino, 1-perhydroazepinyl and 1-perhydroazocinyl.

4. The method of treatment according to claim 1 or 2, wherein for the uracil derivative of formula (I), the 4–8 membered heterocyclic group having 1–3 nitrogen atoms, which is represented by $R^2$ and may be substituted by one or more lower alkyl, imino, hydroxyl, hydroxy methyl, methanesulfonyloxy, amino or nitro groups, is selected from the group consisting of 1-azetidinyl, 1-pyrrolidinyl, 2,5-dimethylpyrrolidin-lyl, 2-iminopyrrolidin-1-yl, 3-hydroxypyrrolidin-1-yl, 2-hydroxymethylpyrrolidin- 1-yl, 3-methanesulfonyloxy pyrrolidin-1-yl, 3-aminopyrrolidin-1-yl, 1-pyrrolyl, 2-pyrazolin-1-yl, 1-pyrazolyl, 2-iminoimidazolidin-1-yl, 2-imino-3-methylimidazolidin-1-yl, 2-imino-3-ethyl imidazolidin-1-yl, 2-imino-3-isopropylimidazolidin-1-yl, 2-imidazolin-1-yl, 2-imino-3-methyl-4-imidazolin-1-yl, 2-imino-3-ethyl-4-imidazolin-1-yl, 1-imidazolyl, 2methylimidazol-1-yl, 2-nitroimidazol-1-yl, 4-nitro-imidazol-1-yl, 1,2,3 -triazol-1-yl, 1,2,4-triazol-1-yl, 3-nitro-1,2,4-triazol-1-yl, piperidino, 4-methyl-piperazin-1-yl, morpholino, 1-perhydroazepinyl and 1-perhydroazocinyl.

5. The method of treatment according to claim 1 or 2, wherein for the uracil derivative of formula (I), the group represented by $R^2$ is selected from the group consisting of 1-azetidinyl, 1-pyrrolidinyl, 2-iminopyrrolidin-1-yl, 2-iminoimidazolidin- 1-yl, 2-imino-3-methylimidazolidin-1-yl, 2-imino-3-ethyl-imidazolidin-1-yl, 2-imino-3-isopropylimidazolidin-1-yl, 2-imidazolin-1-yl, 2-imino-3-methyl-4-imidazolin-1-yl, 2-imino-3-ethyl-4-imidazolin-1-yl, 1-imidazolyl, amidinothio, $N^1$-methylamidinothio, $N^1$, $N^2$-dimethyl amidinothio, 1-guanidino, 1-methylguanidino, 3-methyl-guanidino, 2,3-dimethylguanidino and acetoamidino.

6. The method of treatment according to claim 1, wherein for the uracil derivative of formula (I), the group represented by $R^1$ is a chlorine or bromine atom or a cyano group, and the group represented by $R^2$ is 1-pyrrolidinyl, 1-azetidinyl, 2-iminopyrrolidin-1-yl, 2-iminoimidazolidin-1-yl, 1-imidazolyl, amidinothio or 1-guanidino.

7. The method of treatment according to claim 1, wherein for the uracil derivative of formula (I) is selected from the group consisting of 5-chloro-6-(1-pyrrolidinylmethyl)uracil, 5-bromo-6-(1-pyrrolidinyl methyl)uracil, 5-chloro-6-(1-azetidinylmethyl)uracil, 5-chloro-6-(1-(2-iminopyrrolidinyl)methyl) uracil hydrochloride, 5-bromo-6-(1-(2-iminopyrrolidinyl)methyl)-uracil hydrochloride, 5-cyano-6-(1-(2-iminopyrrolidinyl)methyl)uracil, 5-chloro-6(1-(2-iminoimidazolidinyl)methyl)uracil, 5-bromo-6-(1-(2-iminoimidazolidinyl)methyl)uracil, 5-chloro-6-(1-imidazolylmethyl)uracil hydrochloride, 2-(5-chloro-uracil-6-ylmethyl)isothiourea hydrochloride, 2-(5cyanouracil-6-ylmethyl)isothiourea hydrochloride and 5-chloro-6-(1-guanidino)methyluracil hydrochloride.

* * * * *